United States Patent
Namba et al.

(10) Patent No.: US 9,855,513 B2
(45) Date of Patent: Jan. 2, 2018

(54) METHOD FOR PRODUCING CONCENTRATED AQUEOUS SOLUTION OF ORGANIC COMPOUND

(71) Applicant: Kao Corporation, Tokyo (JP)

(72) Inventors: Masanori Namba, Wakayama (JP); Junnosuke Saito, Osaka (JP)

(73) Assignee: KAO CORPORATION, Tokyo (JP)

( * ) Notice: Subject to any disclaimer, the term of this patent is extended or adjusted under 35 U.S.C. 154(b) by 431 days.

(21) Appl. No.: 14/409,915

(22) PCT Filed: Jun. 7, 2013

(86) PCT No.: PCT/JP2013/003604
§ 371 (c)(1),
(2) Date: Dec. 19, 2014

(87) PCT Pub. No.: WO2013/190794
PCT Pub. Date: Dec. 27, 2013

(65) Prior Publication Data
US 2015/0151213 A1    Jun. 4, 2015

(30) Foreign Application Priority Data
Jun. 19, 2012  (JP) .................................. 2012-137907

(51) Int. Cl.
*B01D 1/00* (2006.01)
*B01D 17/02* (2006.01)
(Continued)

(52) U.S. Cl.
CPC ............. *B01D 1/00* (2013.01); *B01D 1/0017* (2013.01); *B01D 3/006* (2013.01); *B01D 17/02* (2013.01);
(Continued)

(58) Field of Classification Search
CPC . B01D 1/00; B01D 3/00; B01D 3/006; B01D 17/00; B01D 17/02; B01D 17/0205;
(Continued)

(56) References Cited

U.S. PATENT DOCUMENTS 2,400,409 A * 5/1946 Hale ........................ C07C 1/24
585/610
5,395,592 A * 3/1995 Bolleman ............. B06B 1/0292
210/748.02
(Continued)

FOREIGN PATENT DOCUMENTS

CN    101094711 A    12/2007
CN    101247870 A    8/2008
(Continued)

OTHER PUBLICATIONS

International Preliminary Report on Patentability and English translation of the Written Opinion of the International Searching Authority (Forms PCT/IB/338, PCT/IB/373 and PCT/ISA/237), dated Dec. 31, 2014, for International Application No. PCT/JP2013/003604.
(Continued)

*Primary Examiner* — Joseph Drodge
(74) *Attorney, Agent, or Firm* — Birch, Stewart, Kolasch & Birch, LLP

(57) ABSTRACT

After an aqueous solution containing, at a concentration of less than 40% by mass, an organic compound having two or more hydrophilic groups in a molecule is adjusted to contain the organic compound at a concentration of equal to or greater than 40% by mass, the aqueous solution whose organic compound concentration is adjusted to equal to or greater than 40% by mass is irradiated with an ultrasonic wave to atomize water, and is dehydrated and concentrated.

17 Claims, 4 Drawing Sheets

Figure 1:
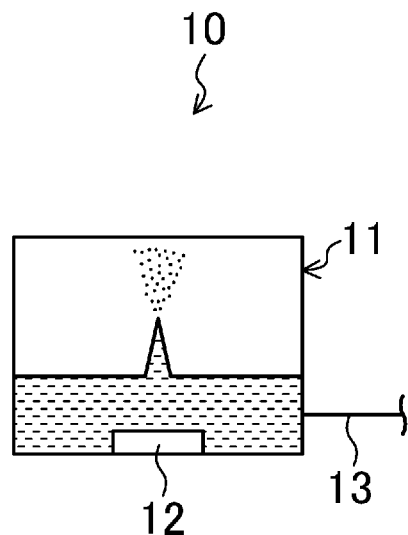

(51) Int. Cl.
*B01J 19/10* (2006.01)
*C02F 1/36* (2006.01)
*C07C 7/00* (2006.01)
*B01D 3/00* (2006.01)

(52) U.S. Cl.
CPC .............. *B01J 19/10* (2013.01); *C02F 1/36* (2013.01); *C07C 7/005* (2013.01); *B01J 2219/0877* (2013.01)

(58) Field of Classification Search
CPC ....... B01D 1/0017; B01D 1/0029; C02F 1/30; C02F 1/36; C02F 2103/34; C02F 2103/36; B01J 19/08; B01J 19/10; B01J 2219/00932; B01J 2219/0877; C07C 7/00; C07C 7/005; C07C 7/10; C07C 27/26
USPC ............ 204/157.15, 157.62, 158.2; 210/634, 210/638, 748.01, 748.02, 770; 560/78, 560/90, 191, 218; 568/700, 913, 916, 568/918, 950, 958
See application file for complete search history.

(56) References Cited

U.S. PATENT DOCUMENTS 7,834,225 B1* 11/2010 Adiga .................. B05B 7/0012
568/913
2005/0016380 A1* 1/2005 Matsuura ................. B01D 3/06
96/389
2007/0295595 A1* 12/2007 Matsuura ............. B01D 1/0017
204/158.2
2008/0000842 A1* 1/2008 Matsuura ................. B01D 1/16
210/748.02
2009/0050550 A1* 2/2009 Matsuura ............... B01D 3/346
210/151

FOREIGN PATENT DOCUMENTS

| | | |
|---|---|---|
| EP | 2213351 A1 | 8/2010 |
| JP | 7-185203 A | 7/1995 |
| JP | 2002-224502 A | 8/2002 |
| JP | 2010-115165 A | 5/2010 |
| JP | 2010-233543 A | 10/2010 |
| JP | 2012-96206 A | 5/2012 |
| JP | 2012-144530 A | 8/2012 |
| WO | WO 2012/086191 A1 | 6/2012 |

OTHER PUBLICATIONS

International Search Report, issued in PCT/JP2013/003604, dated Sep. 10, 2013.
Written Opinion of the International Searching Authority, issued in PCT/JP2013/003604, dated Sep. 10, 2013.

* cited by examiner

METHOD FOR PRODUCING CONCENTRATED AQUEOUS SOLUTION OF ORGANIC COMPOUND

TECHNICAL FIELD

The present invention relates to the method for producing a concentrated aqueous solution of an organic compound and to the dehydration concentration method.

BACKGROUND ART

Research and development have been made on the dehydration technique of atomizing water by irradiating an aqueous solution of an organic compound with an ultrasonic wave.

For example, Patent Documents 1 and 2 disclose the technique of separating lactic acid by irradiating a fermented product of a plant material with an ultrasonic wave and atomizing water.

Moreover, Patent Document 3 discloses the method for producing concentrated glycerol, which includes dehydration concentration of a glycerol aqueous solution having a viscosity of equal to or less than 25 mPa·s by irradiating the glycerol aqueous solution with an ultrasonic wave and atomizing water.

CITATION LIST

Patent Document

PATENT DOCUMENT 1: Japanese Unexamined Patent Publication No. 2010-115165
PATENT DOCUMENT 2: Japanese Unexamined Patent Publication No. 2010-233543
PATENT DOCUMENT 3: Japanese Unexamined Patent Publication No. 2012-144530

SUMMARY OF THE INVENTION

The present invention is intended for the method for producing a concentrated aqueous solution of an organic compound, which includes a concentration adjustment step of adjusting an aqueous solution containing the organic compound at a concentration of less than 40% by mass to contain the organic compound at a concentration of equal to or greater than 40% by mass, the organic compound having two or more hydrophilic groups in a molecule; and a dehydration concentration step of irradiating the aqueous solution whose organic compound concentration is adjusted to equal to or greater than 40% by mass at the concentration adjustment step with an ultrasonic wave to atomize water.

The present invention is intended for the dehydration concentration method including a step of adjusting an aqueous solution containing an organic compound at a concentration of less than 40% by mass to contain the organic compound at a concentration of equal to or greater than 40% by mass, the organic compound having two or more hydrophilic groups in a molecule; and a step of irradiating the aqueous solution whose organic compound concentration is adjusted to equal to or greater than 40% by mass with an ultrasonic wave to atomize water.

BRIEF DESCRIPTION OF THE DRAWINGS

FIG. 1 is a block diagram illustrating the configuration of an ultrasonic atomizer used in a first aspect.

FIG. 2 is a block diagram illustrating the configuration of an ultrasonic atomizer used in second and third aspects.

FIG. 3 is a block diagram illustrating the configuration of an ultrasonic atomizer used in Aspects 2A and 3A.

FIGS. 4A to 4C are block diagrams illustrating another ultrasonic atomizer used in Aspects 2A and 3A.

FIG. 5 is a block diagram illustrating the configuration of an experimental ultrasonic atomizer used in examples.

DESCRIPTION OF EMBODIMENTS

An embodiment will be described in detail below.

The method for producing a concentrated aqueous solution of an organic compound according to the present embodiment includes a concentration adjustment step and a dehydration concentration step. At the concentration adjustment step, an aqueous solution containing an organic compound having two or more hydrophilic groups in a molecule (such an organic compound is hereinafter referred to as an "organic compound A" in the present application) at a concentration of less than 40% by mass is used as a raw material aqueous solution, and the raw material aqueous solution is adjusted such that the concentration of the organic compound A becomes equal to or greater than 40% by mass. At the dehydration concentration step, dehydration concentration is performed in such a manner that the aqueous solution adjusted such that the concentration of the organic compound A becomes equal to or greater than 40% by mass at the concentration adjustment step (such an aqueous solution is hereinafter referred to as a "high-concentration raw material aqueous solution" in the present application) is irradiated with an ultrasonic wave to atomize water.

The present inventors have found the following. In the case where dehydration concentration is performed by irradiating the aqueous solution of the organic compound having two or more hydrophilic groups in the molecule with an ultrasonic wave and atomizing water, the concentration of the organic compound contained in mist drops generated in ultrasonic wave irradiation increases as the concentration of the organic compound in the aqueous solution increases to a certain concentration limit. When the concentration of the organic compound in the aqueous solution irradiated with the ultrasonic wave exceeds the concentration limit, the concentration of the organic compound contained in the mist drops generated in ultrasonic wave irradiation decreases. Moreover, the present inventors have also found that, in the case where the organic compound has two or more hydrophilic groups in the molecule, if the concentration of the organic compound in the aqueous solution is equal to or greater than 40% by mass, the concentration of the organic compound contained in the mist drops generated in ultrasonic wave irradiation is extremely low.

Although the reasons why the concentration of the organic compound contained in the mist drops is low as just described are not clear, the following reasons are assumed. Since the organic compound having two or more hydrophilic groups in the molecule has many hydrophilic groups, the molecules of such an organic compound interacting with each other are more than those of an organic compound having a single hydrophilic group in a molecule, and interaction between the organic compounds each having two or more hydrophilic groups in the molecule is stronger than that between the organic compounds each having a single hydrophilic group in the molecule. Thus, it is difficult to atomize the organic compound having two or more hydrophilic groups in the molecule. Moreover, when the concentration of the organic compound in the aqueous solution increases, the frequency of interaction between the organic compounds is higher than that of interaction between the organic compound and water, resulting in difficulty in atomization. Because of the synergy of these factors, in the case of the organic compound having two or more hydrophilic groups in the molecule, if the concentration of the organic compound in the aqueous solution is equal to or greater than 40% by mass, the concentration of the organic compound contained in the mist drops generated in ultrasonic wave irradiation is extremely low, and water is selectively removed from the aqueous solution. As a result, the efficiency of dehydration concentration by ultrasonic wave irradiation can be enhanced.

According to the method for producing the concentrated aqueous solution of the organic compound in the present embodiment, the concentration of the organic compound A in the raw material aqueous solution is, before dehydration concentration, adjusted from less than 40% by mass to equal to or greater than 40% by mass. Accordingly, the concentration of the organic compound A contained in mist drops generated in irradiation of the high-concentration raw material aqueous solution whose concentration is adjusted with an ultrasonic wave decreases, and water is selectively removed from the high-concentration raw material aqueous solution. As a result, the efficiency of dehydration concentration by ultrasonic wave irradiation, i.e., the efficiency of dehydration per energy in ultrasonic wave irradiation, can be enhanced.

<Raw Material Aqueous Solution>

The raw material aqueous solution contains the organic compound A having two or more hydrophilic groups in the molecule.

From the viewpoint of a high efficiency of dehydration concentration by ultrasonic wave irradiation, the number of carbon atoms in the molecule of the organic compound A is preferably two or more, and more preferably three or more. From the viewpoint of solubility in water, the number of carbon atoms in the molecule of the organic compound A is preferably 22 or less, more preferably 12 or less, and much more preferably 6 or less.

From the viewpoint of a high efficiency of dehydration concentration by ultrasonic wave irradiation, the molecular weight of the organic compound A is preferably 50 or more, more preferably 60 or more, and much more preferably 70 or more. From the viewpoint of solubility in water, the molecular weight of the organic compound A is preferably 400 or less, more preferably 300 or less, and much more preferably 200 or less.

The organic compound A has two or more hydrophilic groups in the molecule. The hydrophilic group is a functional group forming a weak bond to a water molecule by, e.g., electrostatic interaction or hydrogen bonding and having ionicity or high polarity showing affinity for water. Specifically, examples of the hydrophilic group include a hydroxyl group, a carboxyl group, a carbonyl group, an ester group, an acetal group, a hemiacetal group, an ether group, an amino group, an ammonium group, an amide group, a sulfonate group, a sulfate ester group, a phosphonate group, a phosphate group, and an ureido group.

From the viewpoint of a high efficiency of dehydration concentration by ultrasonic wave irradiation, the hydrophilic group includes one or more chosen from the group consisting of a hydroxyl group, a carboxyl group, a carbonyl group, an acetal group, a hemiacetal group, an amino group, an ammonium group, a sulfonate group, a sulfate ester group, a phosphonate group, or a phosphate group. More preferably, the hydrophilic group includes one or more chosen from the group consisting of a hydroxyl group, a carboxyl group, a carbonyl group, an acetal group, a hemiacetal group, an amino group, or a sulfonate group. Much more preferably, the hydrophilic group includes one or more chosen from the group consisting of a hydroxyl group or a carboxyl group.

The number of hydrophilic groups in the molecule of the organic compound A is two or more from the viewpoint of a high efficiency of dehydration concentration by ultrasonic wave irradiation. From the viewpoint of a high efficiency of dehydration concentration by ultrasonic wave irradiation and an economic efficiency, the number of hydrophilic groups in the molecule of the organic compound A is preferably 10 or less, more preferably 8 or less, much more preferably 5 or less, and still much more preferably 3 or less.

In the organic compound A, a plurality of hydrophilic groups may be bonded to the same carbon atom, or may be bonded respectively to adjacent carbon atoms or to carbon atoms positioned with, e.g., one or more methylene groups being interposed therebetween. Alternatively, the organic compound A may have both of the foregoing characteristics. Of these organic compounds A, the organic compound formed such that a plurality of hydrophilic groups are bonded to the same carbon atom or the organic compound formed such that a plurality of hydrophilic groups are bonded respectively to adjacent carbon atoms are preferable.

The organic compound A may have two or more of a single type of hydrophilic group in the molecule, or may have two or more types of hydrophilic group in the molecule. Alternatively, the organic compound A may have both of the foregoing characteristics.

In the case of an optional organic compound A formed to have compatibility with water, dehydration concentration by ultrasonic wave irradiation produces a prominent effect. From the viewpoint of a high efficiency of dehydration concentration by ultrasonic wave irradiation, the degree of solubility (hereinafter abbreviated as a "solubility degree") of the organic compound A in a water of 100 g at 25° C. is preferably 67 g or more, more preferably 100 g or more, and much more preferably 150 g or more. Still much more preferably, the solubility degree of the organic compound A is such a degree that the organic compound A can dissolve in water at any ratio.

Examples of the organic compound A having two or more of a single type of hydrophilic group in the molecule include polyhydric alcohol having two or more hydroxyl groups, polyhydric carboxylic acid having two or more carboxyl groups, and polyhydric amine having two or more amino groups.

Examples of polyhydric alcohol include diols each having two hydroxyl groups in a molecule, such as ethylene glycol, diethylene glycol, 1,2-propanediol (propylene glycol), and 1,3-propanediol; triols each having three hydroxyl groups in a molecule, such as glycerol, trimethylolpropane, and 1,2,4-butanetriol; tetraols each having four hydroxyl groups in a molecule, such as pentaerythritol; and sugars such as glucose and xylose.

Examples of polyhydric carboxylic acid include dicarboxylic acids such as oxalic acid, malonic acid, succinic acid, maleic acid, fumaric acid, phthalic acid, isophthalic acid, terephthalic acid, and furandicarboxylic acid; tricarboxylic acids such as citric acid, trimellitic acid (benzene-1,2,4-tricarboxylic acid), and benzene-1,3,5-tricarboxylic acid; and tetracarboxylic acids such as ethylene tetracarboxylic acid and benzene-1,2,4,5-tetracarboxylic acid.

Examples of polyhydric amine include diamines such as ethylenediamine and paraphenylene diamine; triamines such as diethylenetriamine; and tetraamines such as triethylenetetramine.

Examples of the organic compound A having two or more types of hydrophilic group in the molecule include hydroxy acid having a hydroxyl group and a carboxyl group, amino acid having a carboxyl group and an amino group, and hydroxy aldehyde having a hydroxyl group and a carbonyl group.

Hydroxy acid may be α-hydroxy acids in each of which a hydroxyl group and a carboxyl group are bonded to the same carbon atom, such as lactic acid and 2-hydroxybutyric acid; β-hydroxy acids in each of which a hydroxyl group and a carboxyl group are bonded respectively to different carbon atoms, such as 3-hydroxybutyric acid; or γ-hydroxy acids in each of which a hydroxyl group and a carboxyl group are bonded respectively to different carbon atoms, such as 4-hydroxybutyric acid.

Hydroxy acid may be aliphatic hydroxy acid or aromatic hydroxy acid. Examples of aliphatic hydroxy acid include 2-hydroxybutyric acid, glycolic acid, lactic acid, glyceric acid, malic acid, tartaric acid, and citric acid. Examples of aromatic hydroxy acid include salicylic acid.

Amino acid may be α-amino acids in each of which a carboxyl group and an amino group are bonded to the same carbon atom, such as glycine, α-alanine, glutamine, glutamic acid, and aspartic acid; β-amino acids in each of which a carboxyl group and an amino group are bonded respectively to different carbon atoms, such as β-alanine; or γ-amino acids in each of which a carboxyl group and an amino group are bonded respectively to different carbon atoms, such as γ-aminobutyric acid.

Amino acid may be aliphatic amino acid or aromatic amino acid. Examples of aliphatic amino acid include glycine, alanine, glutamic acid, and aspartic acid. Examples of aromatic amino acid include phenylalanine.

Examples of hydroxy aldehyde include hydroxymethylfurfural.

Of these compounds, polyhydric alcohol having two or more hydroxyl groups, hydroxy acid having a hydroxyl group and a carboxyl group, hydroxy aldehyde having a hydroxyl group and a carbonyl group, or heterocyclic aldehyde having a heterocycle and a carbonyl group is preferably used from the viewpoint of a high efficiency of dehydration concentration by ultrasonic wave irradiation. More preferably, glycerol (a solubility degree of ∞), lactic acid (a solubility degree of equal to or greater than 614 g), glucose (a solubility degree of 91 g), or hydroxymethylfurfural (a solubility degree of co) is used.

Although the concentration of the organic compound A in the raw material aqueous solution is less than 40% by mass, the concentration of the organic compound A in the raw material aqueous solution is, from the viewpoint of a high efficiency at the concentration adjustment step, preferably equal to or less than 35% by mass, more preferably equal to or less than 30% by mass, much more preferably equal to or less than 25% by mass, and still much more preferably equal to or less than 20% by mass. From the same viewpoint as above, the concentration of the organic compound A in the raw material aqueous solution is equal to or greater than 0.1% by mass, preferably equal to or greater than 0.5% by mass, more preferably equal to or greater than 1% by mass, much more preferably equal to or greater than 3% by mass, and still much more preferably 5% by mass.

Note that a component(s) to be removed from the raw material aqueous solution or a component(s) remaining in the raw material aqueous solution after ultrasonic wave irradiation, such as methanol, may be contained together with the organic compound A in the raw material aqueous solution within such a range that effectiveness in enhancement of a dehydration concentration efficiency by ultrasonic wave irradiation is not reduced.

<Concentration Adjustment Step>

The method for adjusting the raw material aqueous solution containing the organic compound A at a concentration of less than 40% by mass to the high-concentration raw material aqueous solution containing the organic compound A at a concentration of equal to or greater than 40% by mass is not limited.

Examples of the concentration adjustment method include (a) the method for mixing a raw material aqueous solution containing an organic compound A at a concentration of less than 40% by mass with an organic compound A or with an aqueous solution containing an organic compound A at a concentration of greater than 40% by mass (such an aqueous solution is hereinafter also referred to as a "high-concentration aqueous solution"); and (b) the method for dehydrating and concentrating a raw material aqueous solution containing an organic compound A at a concentration of less than 40% by mass. The method (a) is preferable from the viewpoint of a high process efficiency.

In the method (a), the concentration of the organic compound A in the high-concentration aqueous solution is, from the viewpoint of a high efficiency of concentration adjustment of the raw material aqueous solution, preferably equal to or greater than 45% by mass, more preferably equal to or greater than 50% by mass, and much more preferably equal to or greater than 60% by mass. From the viewpoint of a high efficiency of dehydration concentration by ultrasonic wave irradiation and easiness in preparing the high-concentration aqueous solution, the concentration of the organic compound A in the high-concentration aqueous solution is equal to or less than 99% by mass, preferably equal to or less than 95% by mass, more preferably equal to or less than 90% by mass, much more preferably equal to or less than 80% by mass, and still much more preferably equal to or less than 70% by mass.

From the viewpoint of a high process efficiency in the method for producing the concentrated aqueous solution of the organic compound according to the present embodiment, the product formed by such a process, i.e., the concentrated aqueous solution of the organic compound A formed by dehydration concentration using ultrasonic wave irradiation, is preferably used as the high-concentration aqueous solution.

In the method (b), the concentration of the high-concentration raw material aqueous solution may be adjusted in such a manner that the concentration of the organic compound A is increased to equal to or greater than 40% by mass by dehydration concentration of the raw material aqueous solution. The dehydration concentration step may include ultrasonic wave irradiation, or may include, e.g., moisture evaporation by heating.

At the concentration adjustment step, the high-concentration raw material aqueous solution adjusted, by the method (a) or (b), so as to contain the organic compound A at a concentration of equal to or greater than 40% by mass may be supplied into an atomization tank provided with an ultrasonic oscillator. Alternatively, concentration adjustment may be performed by the method (a) or (b) in an ultrasonic atomizer including an atomization tank provided with an ultrasonic oscillator.

From the viewpoint of a high efficiency of dehydration concentration by ultrasonic wave irradiation, the concentration of the organic compound A in the high-concentration raw material aqueous solution after concentration adjustment is preferably equal to or greater than 45% by mass, more preferably equal to or greater than 50% by mass, and much more preferably equal to or greater than 60% by mass. From the same viewpoint as above, the concentration of the organic compound A in the high-concentration raw material aqueous solution after concentration adjustment is equal to or less than 99% by mass, preferably equal to or less than 95% by mass, more preferably equal to or less than 90% by mass, much more preferably equal to or less than 80% by mass, and still much more preferably equal to or less than 70% by mass.

<Dehydration Concentration Step>

When the high-concentration raw material aqueous solution whose concentration is adjusted is irradiated with an ultrasonic wave, a liquid pillar of the high-concentration raw material aqueous solution stands at a liquid surface, and water is atomized from the liquid pillar. As a result, the high-concentration raw material aqueous solution is dehydrated and concentrated. Note that the dehydration concentration step may be performed at a certain time interval after the concentration adjustment step, or may be performed concurrently with the concentration adjustment step.

From the viewpoint of a high efficiency of dehydration concentration by ultrasonic wave irradiation, the frequency of ultrasonic vibrations applied to the high-concentration raw material aqueous solution is preferably equal to or higher than 20 kHz, and more preferably equal to or higher than 1 MHz. From the same viewpoint as above, the frequency of ultrasonic vibrations applied to the high-concentration raw material aqueous solution is preferably equal to or lower than 10 MHz, and more preferably equal to or lower than 5 MHz. The high-concentration raw material aqueous solution can be irradiated with an ultrasonic wave by the ultrasonic oscillator provided in the atomization tank capable of storing the high-concentration raw material aqueous solution.

The temperature of the high-concentration raw material aqueous solution in ultrasonic wave irradiation is not limited as long as the high-concentration raw material aqueous solution is in a liquid form. From the viewpoint of a high efficiency of atomization by ultrasonic wave irradiation and reduction in energy consumption, the temperature of the high-concentration raw material aqueous solution in ultrasonic wave irradiation is equal to or higher than 10° C., preferably equal to or higher than 20° C., more preferably equal to or higher than 30° C., much more preferably equal to or higher than 40° C., and still much more preferably equal to or higher than 50° C. From the viewpoint of reduction in facility load such as pressurization and temperature control, the temperature of the high-concentration raw material aqueous solution in ultrasonic wave irradiation is preferably equal to or lower than 100° C., more preferably equal to or lower than 90° C., much more preferably equal to or lower than 80° C., still much more preferably equal to or lower than 70° C. The temperature of the high-concentration raw material aqueous solution can be controlled by a temperature control mechanism attached to the atomization tank capable of storing the high-concentration raw material aqueous solution.

Liquid drops atomized from the high-concentration raw material aqueous solution by ultrasonic wave irradiation can be discharged with carrier gas. Although not limited, e.g., air, nitrogen gas, and other types of inert gas may be used as the carrier gas. The temperature of the carrier gas is not limited as long as there is no significant temperature difference between the carrier gas and the high-concentration raw material aqueous solution irradiated with an ultrasonic wave. However, the carrier gas is preferably at normal temperature or the same temperature as that of the high-concentration raw material aqueous solution.

From the viewpoint of a high efficiency of dehydration concentration by ultrasonic wave irradiation, the concentration of the organic compound A in the high-concentration raw material aqueous solution in ultrasonic wave irradiation is preferably equal to or greater than 40% by mass, more preferably equal to or greater than 45% by mass, much more preferably equal to or greater than 50% by mass, and still much more preferably equal to or greater than 60% by mass. From the same viewpoint as above, the concentration of the organic compound A in the high-concentration raw material aqueous solution in ultrasonic wave irradiation is preferably equal to or less than 99% by mass, more preferably equal to or less than 90% by mass, much more preferably equal to or less than 80% by mass, and still much more preferably equal to or less than 70% by mass. Note that, at the dehydration concentration step, the concentration of the organic compound A in the high-concentration raw material aqueous solution in ultrasonic wave irradiation may fall outside the foregoing concentration range as long as the effectiveness in dehydration concentration by ultrasonic wave irradiation is not influenced.

From the viewpoint of a high efficiency of dehydration concentration by ultrasonic wave irradiation, the concentration of the organic compound A in the atomized liquid drops is equal to or less than 5% by mass, preferably equal to or less than 3% by mass, more preferably equal to or less than 1% by mass, much more preferably equal to or less than 0.5% by mass, and still much more preferably equal to or less than 0.25% by mass.

From the viewpoint of a high efficiency of dehydration concentration by ultrasonic wave irradiation, the viscosity of the high-concentration raw material aqueous solution in ultrasonic wave irradiation is, at the temperature in ultrasonic wave irradiation, preferably equal to or less than 25 mPa·s, more preferably equal to or less than 20 mPa·s, and much more preferably equal to or less than 15 mPa·s. From the same viewpoint as above, the viscosity of the high-concentration raw material aqueous solution in ultrasonic wave irradiation is, at a more-preferable temperature of 50° C., preferably equal to or less than 25 mPa·s, more preferably equal to or less than 20 mPa·s, and much more preferably 15 mPa·s. The viscosity of the high-concentration raw material aqueous solution in ultrasonic wave irradiation can be obtained with reference to ISO 12058 published by the International Organization for Standardization. Specifically, the viscosity of the high-concentration raw material aqueous solution can be obtained based on a time required for a ball to fall, due to the gravity, in an inclined capillary filled with the high-concentration raw material aqueous solution.

From the viewpoint of a high efficiency of dehydration concentration by ultrasonic wave irradiation, the concentration of the organic compound A in the concentrated aqueous solution after dehydration concentration is preferably equal to or greater than 40% by mass, more preferably equal to or greater than 45% by mass, much more preferably equal to or greater than 50% by mass, and still much more preferably equal to or greater than 60% by mass. From the viewpoint of reduction in environmental load and a high economic efficiency, the concentration of the organic compound A in the concentrated aqueous solution after dehydration concentration is preferably equal to or less than 100% by mass, more preferably equal to or less than 98% by mass, and much more preferably equal to or less than 95% by mass.

From the viewpoint of economic dehydration concentration by ultrasonic wave irradiation, the viscosity of the concentrated aqueous solution after dehydration concentration is, at the temperature in ultrasonic wave irradiation, preferably equal to or less than 25 mPa·s, more preferably equal to or less than 20 mPa·s, and much more preferably equal to or less than 15 mPa·s. From the same viewpoint as above, the viscosity of the concentrated aqueous solution after dehydration concentration is, at a more-preferable temperature of 50° C., preferably equal to or less than 25 mPa·s, more preferably equal to or less than 20 mPa·s, and much more preferably equal to or less than 15 mPa·s.

<Recovery Step>

The method for producing the concentrated aqueous solution of the organic compound according to the present embodiment may further include a recovery step of recovering the aqueous solution of the organic compound A dehydrated and concentrated at the dehydration concentration step.

The recovery step may be performed after the dehydration concentration step, may be performed concurrently with the dehydration concentration step, or may be performed concurrently with the concentration adjustment step and the dehydration concentration step. Since the recovery step is performed concurrently with the dehydration concentration step or with the concentration adjustment step and the dehydration concentration step, the concentrated aqueous solution of the organic compound A can be continuously produced. At the recovery step, the concentrated aqueous solution may be continuously or intermittently recovered.

Note that the concentrated aqueous solution of the organic compound A recovered at the recovery step can be, as described above, used as the high-concentration aqueous solution used for concentration adjustment at the concentration adjustment step.

(Specific Aspects)

Specific Aspects of the method for producing the concentrated aqueous solution of the organic compound according to the present embodiment will be described.

<First Aspect: Batch Operation>

In a batch operation (i) of the first aspect, an ultrasonic atomizer 10 illustrated in FIG. 1 is used to mix, outside an atomization tank 11, a raw material aqueous solution containing an organic compound A at a concentration of less than 40% by mass with an organic compound A or with a high-concentration aqueous solution containing an organic compound A at a concentration of greater than 40% by mass, thereby preparing a high-concentration raw material aqueous solution adjusted so as to contain the organic compound A at a concentration of equal to or greater than 40% by mass. Alternatively, a raw material aqueous solution is dehydrated and concentrated to prepare a high-concentration raw material aqueous solution adjusted so as to contain an organic compound A at a concentration of equal to or greater than 40% by mass. Then, the high-concentration raw material aqueous solution is supplied into the atomization tank 11 of the ultrasonic atomizer 10 (the concentration adjustment step). Examples of the dehydration concentration method for concentration adjustment in the latter case include water atomization by ultrasonic wave irradiation, and moisture evaporation by heating. Then, in the atomization tank 11, the high-concentration raw material aqueous solution is irradiated with an ultrasonic wave by an ultrasonic oscillator 12 provided in the atomization tank 11 to atomize water. As a result, the high-concentration raw material aqueous solution is dehydrated and concentrated (the dehydration concentration step).

In a batch operation (ii) of the first aspect, the ultrasonic atomizer 10 illustrated in FIG. 1 is used. An organic compound A or a high-concentration aqueous solution is supplied into the atomization tank 11, and then a raw material aqueous solution is added thereto. In this manner, a high-concentration raw material aqueous solution adjusted so as to contain the organic compound A at a concentration of equal to or greater than 40% by mass is prepared (the concentration adjustment step). Then, in the atomization tank 11, the high-concentration raw material aqueous solution is irradiated with an ultrasonic wave by the ultrasonic oscillator 12 to atomize water. As a result, the high-concentration raw material aqueous solution is dehydrated and concentrated (the dehydration concentration step).

In a batch operation (iii) of the first aspect, the ultrasonic atomizer 10 illustrated in FIG. 1 is used. A raw material aqueous solution is supplied into the atomization tank 11, and then an organic compound A or a high-concentration aqueous solution is added thereto. In this manner, a high-concentration raw material aqueous solution adjusted so as to contain the organic compound A at a concentration of equal to or greater than 40% by mass is prepared (the concentration adjustment step). Then, in the atomization tank 11, the high-concentration raw material aqueous solution is irradiated with an ultrasonic wave by the ultrasonic oscillator 12 to atomize water. As a result, the high-concentration raw material aqueous solution is dehydrated and concentrated (the dehydration concentration step).

In any of the batch operations (i) to (iii) of the first aspect, the concentrated aqueous solution of the organic compound A formed after dehydration concentration may be discharged and recovered through a concentrated aqueous solution discharge pipe 13 extending from the atomization tank 11 (the recovery step).

<Second Aspect: Semi-batch Operation>

[Aspect 2A]

Aspect 2A-(i)

Figure 2:
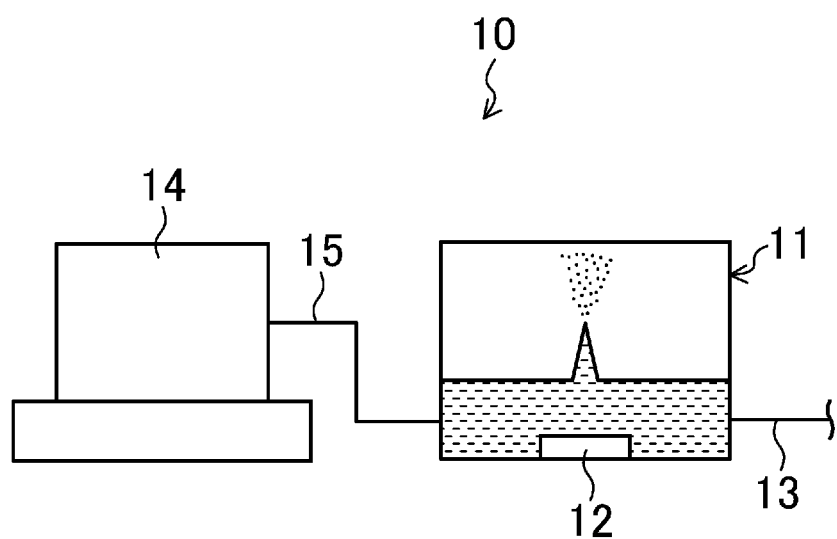
Figure 3:
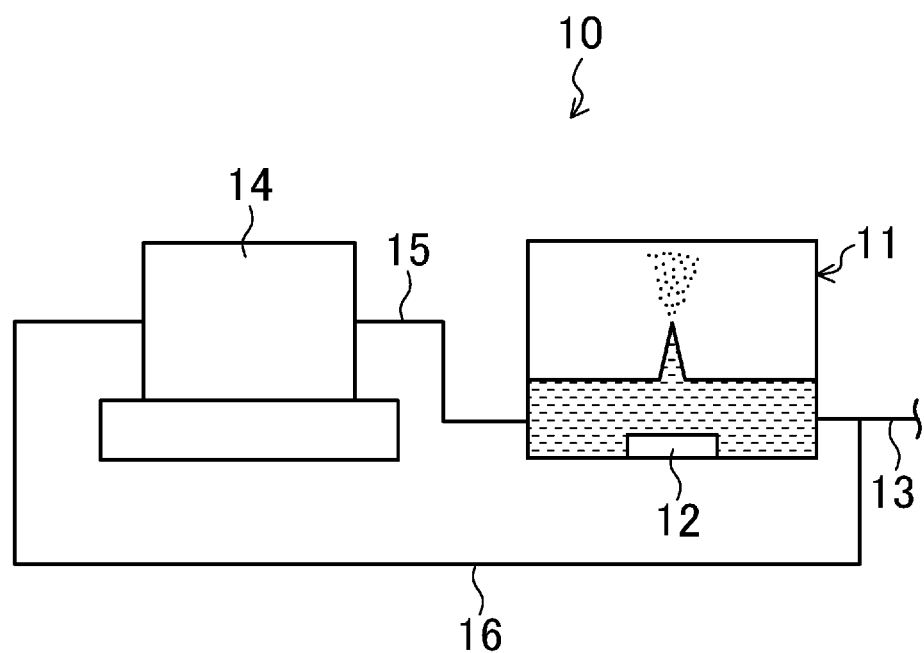

In a semi-batch operation (i) of Aspect 2A, an ultrasonic atomizer 10 illustrated in FIGS. 2 to 4 is used to mix, outside an atomization tank 11, a raw material aqueous solution containing an organic compound A at a concentration of less than 40% by mass with an organic compound A or with a high-concentration aqueous solution containing an organic compound A at a concentration of greater than 40% by mass, thereby preparing a high-concentration raw material aqueous solution adjusted so as to contain the organic compound A at a concentration of equal to or greater than 40% by mass. Alternatively, a raw material aqueous solution is dehydrated and concentrated to prepare a high-concentration raw material aqueous solution adjusted so as to contain an organic compound A at a concentration of equal to or greater than 40% by mass. Then, the high-concentration raw material aqueous solution is directly supplied into the atomization tank 11 of the ultrasonic atomizer 10 (the initial stage of the concentration adjustment step). Examples of the dehydration concentration method for concentration adjustment in the latter case include water atomization by ultrasonic wave irradiation, and moisture evaporation by heating. Independently of the high-concentration raw material aqueous solution initially supplied into the atomization tank 11, a high-concentration raw material aqueous solution is prepared in such a manner that an aqueous solution containing an organic compound A at a concentration of less than 40% by mass is adjusted to contain the organic compound A at a concentration of equal to or greater than 40% by mass (the concentration adjustment step). While such a high-concentration raw material aqueous solution is being continuously or intermittently supplied through a raw material supply pipe 15 which extends from a raw material tank 14 and which is connected to the atomization tank 11, the high-concentration raw material aqueous solution is, in the atomization tank 11, irradiated with an ultrasonic wave by an ultrasonic oscillator 12 provided in the atomization tank 11 to atomize water. As a result, the high-concentration raw material aqueous solution is dehydrated and concentrated (the dehydration concentration step).

In the method for preparing the high-concentration raw material aqueous solution to be supplied to the atomization tank 11 through the raw material supply pipe 15, a raw material aqueous solution may be, outside the raw material tank 14, mixed with an organic compound A or with a high-concentration aqueous solution, thereby preparing a high-concentration raw material aqueous solution containing the organic compound A at a concentration of equal to or greater than 40% by mass. Alternatively, a raw material aqueous solution may be dehydrated and concentrated, thereby preparing a high-concentration raw material aqueous solution adjusted so as to contain an organic compound A at a concentration of equal to or greater than 40% by mass. Then, the high-concentration raw material aqueous solution may be supplied into the raw material tank 14 and stored in the raw material tank 14 (Aspect 2A-(i)-a). The concentration adjustment step of the high-concentration raw material aqueous solution in Aspect 2A-(i)-a may be performed concurrently with the dehydration concentration step. In such a case, part or all of the high-concentration aqueous solution to be mixed with the raw material aqueous solution may be, in the former method, the concentrated aqueous solution of the organic compound A formed at the dehydration concentration step. Examples of the latter dehydration concentration method for concentration adjustment include water atomization by ultrasonic wave irradiation, and moisture evaporation by heating. The high-concentration raw material aqueous solution supplied into the raw material tank 14 may be the same as the high-concentration raw material aqueous solution initially supplied into the atomization tank 11.

An organic compound A or a high-concentration aqueous solution may be supplied into the raw material tank 14, and then a raw material aqueous solution is added to the organic compound A or the high-concentration aqueous solution to prepare a high-concentration raw material aqueous solution adjusted so as to contain the organic compound A at a concentration of equal to or greater than 40% by mass (Aspect 2A-(i)-b). The concentration adjustment step of the high-concentration raw material aqueous solution in Aspect 2A-(i)-b may be performed concurrently with the dehydration concentration step. In such a case, part or all of the high-concentration aqueous solution to be mixed with the raw material aqueous solution may be the concentrated aqueous solution of the organic compound A formed at the dehydration concentration step. For example, the ultrasonic atomizer 10 illustrated in FIG. 3 may be used to supply the concentrated aqueous solution of the organic compound A formed at the dehydration concentration step to the raw material tank 14 through a return pipe 16 which branches from the concentrated aqueous solution discharge pipe 13 and which is connected to the raw material tank 14, and therefore part or all of the high-concentration aqueous solution supplied into the raw material tank 14 may be the concentrated aqueous solution of the organic compound A (Aspect 2A-(i)-b').

A raw material aqueous solution may be supplied into the raw material tank 14, and then an organic compound A or a high-concentration aqueous solution is added to the raw material aqueous solution to prepare a high-concentration raw material aqueous solution adjusted so as to contain the organic compound A at a concentration of equal to or greater than 40% by mass (Aspect 2A-(i)-c). The concentration adjustment step of the high-concentration raw material aqueous solution in Aspect 2A-(i)-c may be performed concurrently with the dehydration concentration step. In such a case, part or all of the high-concentration aqueous solution to be mixed with the raw material aqueous solution may be the concentrated aqueous solution of the organic compound A formed at the dehydration concentration step. For example, the ultrasonic atomizer 10 illustrated in FIG. 3 may be used to supply the concentrated aqueous solution of the organic compound A formed at the dehydration concentration step to the raw material tank 14 through the return pipe 16 which branches from the concentrated aqueous solution discharge pipe 13 and which is connected to the raw material tank 14, and therefore part or all of the high-concentration aqueous solution to be added to the raw material aqueous solution supplied into the raw material tank 14 may be the concentrated aqueous solution of the organic compound A (Aspect 2A-(i)-c').

A raw material aqueous solution may be supplied into the raw material tank 14, and may be dehydrated and concentrated to prepare a high-concentration raw material aqueous solution adjusted so as to contain an organic compound A at a concentration of equal to or greater than 40% by mass (Aspect 2A-(i)-d). Examples of the dehydration concentration method for concentration adjustment include water atomization by ultrasonic wave irradiation, and moisture evaporation by heating.

Such a high-concentration raw material aqueous solution may be prepared in the course of supplying the raw material aqueous solution from the raw material tank 14 to the atomization tank 11 through the raw material supply pipe 15.

For example, the ultrasonic atomizer 10 illustrated in FIG. 4A may be used to supply a raw material aqueous solution into the raw material tank 14. In the course of supplying the raw material aqueous solution to the atomization tank 11 through the raw material supply pipe 15, an organic compound A or a high-concentration aqueous solution may join the raw material aqueous solution through an organic-compound-A supply pipe 17 connected to the raw material supply pipe 15, and therefore a high-concentration raw material aqueous solution adjusted so as to contain the organic compound A at a concentration of equal to or greater than 40% by mass may be prepared (Aspect 2A-(i)-e). The concentration adjustment step of the high-concentration raw material aqueous solution in Aspect 2A-(i)-e is performed concurrently with the dehydration concentration step.

The ultrasonic atomizer 10 illustrated in FIG. 4B may be used to supply a raw material aqueous solution into the raw material tank 14. In the course of supplying the raw material aqueous solution to the atomization tank 11 through the raw material supply pipe 15, the concentrated aqueous solution of the organic compound A formed at the dehydration concentration step may join the raw material aqueous solution through a return pipe 18 which branches from the concentrated aqueous solution discharge pipe 13 and which is connected to the raw material supply pipe 15, and therefore a high-concentration raw material aqueous solution adjusted so as to contain the organic compound A at a concentration of equal to or greater than 40% by mass may be prepared (Aspect 2A-(i)-f). The concentration adjustment step of the high-concentration raw material aqueous solution in Aspect 2A-(i)-f is performed concurrently with the dehydration concentration step. Moreover, the concentrated aqueous solution of the organic compound A formed at the dehydration concentration step is used as the high-concentration aqueous solution to be mixed with the raw material aqueous solution.

Figure 4A:
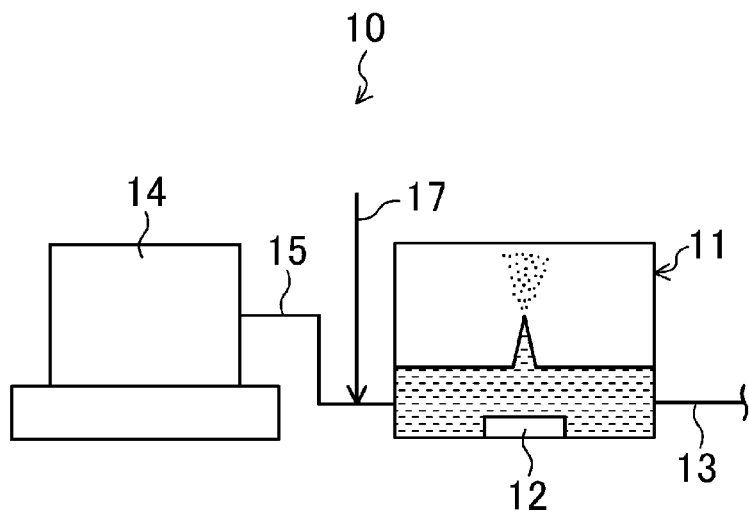
Figure 4B:
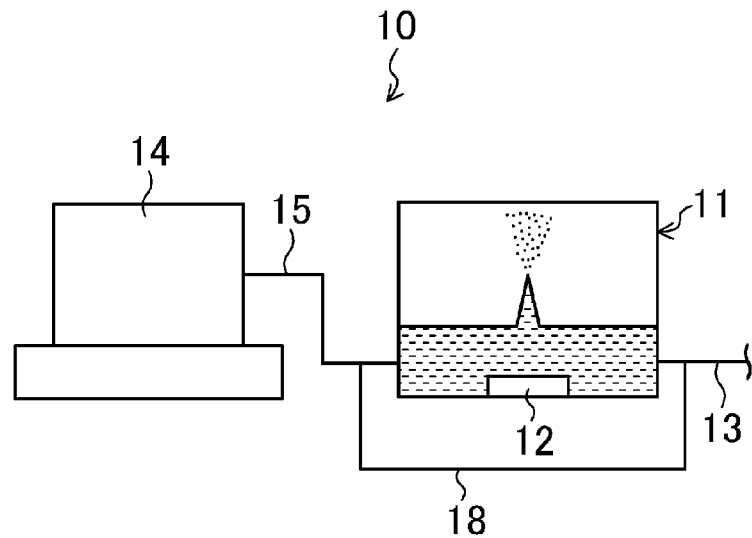
Figure 4C:
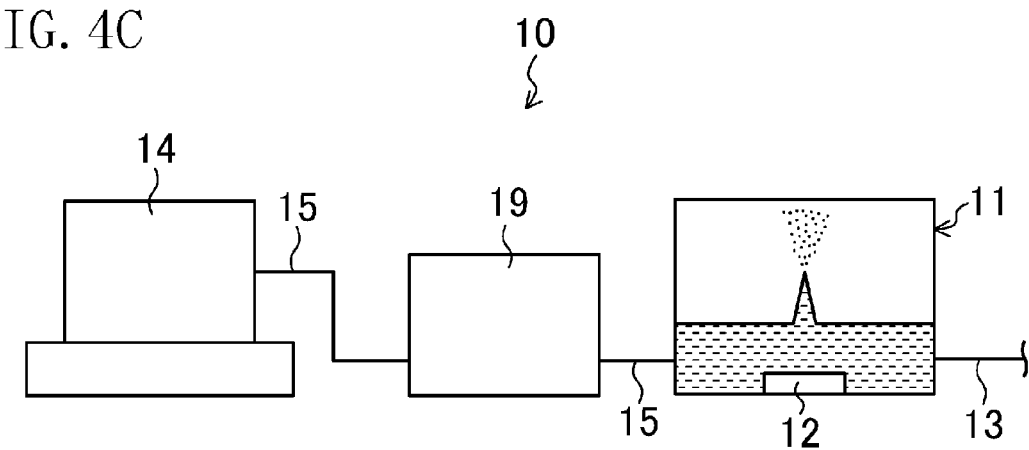
Figure 5:
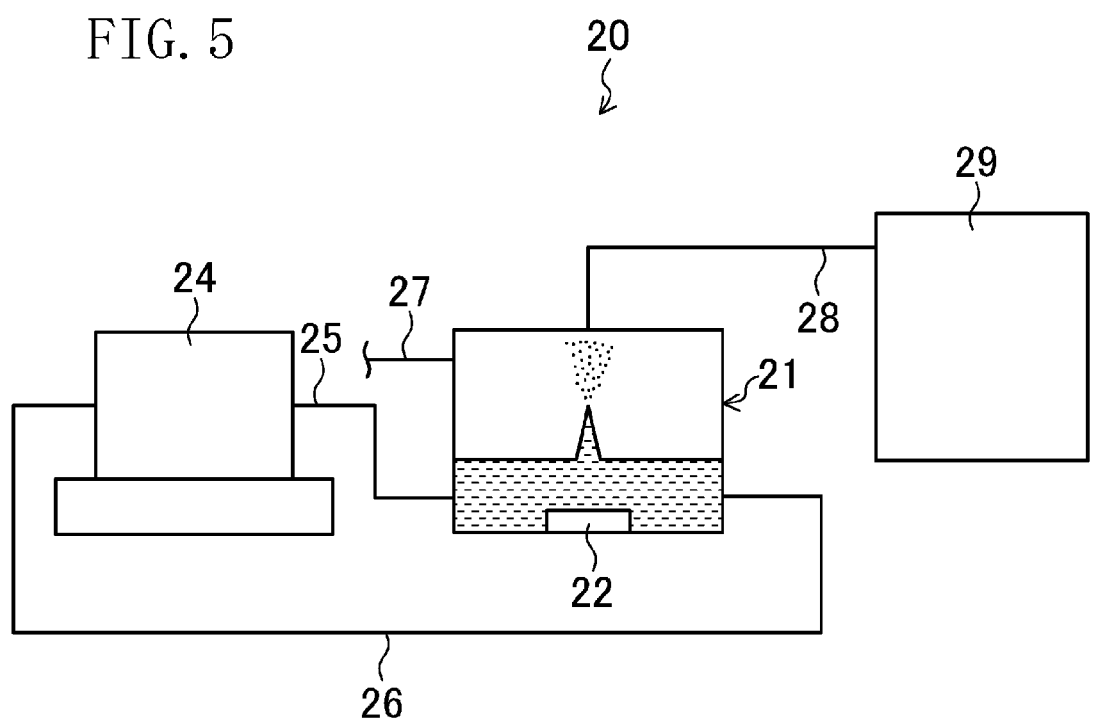

The ultrasonic atomizer 10 illustrated in FIG. 4C may be used to supply a raw material aqueous solution into the raw material tank 14. In the course of supplying the raw material aqueous solution to the atomization tank 11 through the raw material supply pipe 15, a high-concentration raw material aqueous solution adjusted so as to contain an organic compound A at a concentration of equal to or greater than 40% by mass may be prepared in a concentration adjuster 19 provided in the raw material supply pipe 15 (Aspect 2A-(i)-g). The concentration adjustment step of the high-concentration raw material aqueous solution in Aspect 2A-(i)-g is performed concurrently with the dehydration concentration step. Moreover, in the concentration adjuster 19, the concentrated aqueous solution of the organic compound A formed at the dehydration concentration step may be used to perform concentration adjustment.

The concentration adjuster 19 may be an atomization tank in which a raw material aqueous solution is dehydrated and concentrated by ultrasonic atomization. In such a case, atomization tanks each provided with an ultrasonic oscillator are continuously provided. The concentration of a raw material aqueous solution is adjusted in the upstream atomization tank serving as the concentration adjuster 19, and the high-concentration raw material aqueous solution whose concentration is adjusted is dehydrated and concentrated in the downstream atomization tank 11. The concentration adjuster 19 may be a unit other than the dehydration concentration unit using ultrasonic atomization, such as a heating tank capable of evaporating moisture of a raw material aqueous solution by heating to dehydrate and concentrate the raw material aqueous solution.

Aspect 2A-(ii)

In a semi-batch operation (ii) of Aspect 2A, the ultrasonic atomizer 10 illustrated in FIGS. 2 to 4 is used to supply an organic compound A or a high-concentration aqueous solution into the atomization tank 11. A raw material aqueous solution is added to the organic compound A or the high-concentration aqueous solution to prepare a high-concentration raw material aqueous solution adjusted so as to contain the organic compound A at a concentration of equal to or greater than 40% by mass (the initial stage of the concentration adjustment step). Independently of the high-concentration raw material aqueous solution initially supplied into the atomization tank 11, a high-concentration raw material aqueous solution is prepared in such a manner that an aqueous solution containing an organic compound A at a concentration of less than 40% by mass is adjusted to contain the organic compound A at a concentration of equal to or greater than 40% by mass (the concentration adjustment step). While such a high-concentration raw material aqueous solution is being continuously or intermittently supplied through the raw material supply pipe 15, the high-concentration raw material aqueous solution is, in the atomization tank 11, irradiated with an ultrasonic wave by the ultrasonic oscillator 12 to atomize water. As a result, the high-concentration raw material aqueous solution is dehydrated and concentrated (the dehydration concentration step).

Examples of the method for preparing the high-concentration raw material aqueous solution to be supplied to the atomization tank 11 through the raw material supply pipe 15 include the methods of Aspect 2A-(ii)-a, Aspect 2A-(ii)-b, Aspect 2A-(ii)-b', Aspect 2A-(ii)-c, Aspect 2A-(ii)-c', Aspect 2A-(ii)-d, Aspect 2A-(ii)-e, Aspect 2A-(ii)-f, and Aspect 2A-(ii)-g corresponding respectively to Aspect 2A-(i)-a, Aspect 2A-(i)-b, Aspect 2A-(i)-b', Aspect 2A-(i)-c, Aspect 2A-(i)-c', Aspect 2A-(i)-d, Aspect 2A-(i)-e, Aspect 2A-(i)-f, and Aspect 2A-(i)-g.

Aspect 2A-(iii)

In a semi-batch operation (iii) of Aspect 2A, the ultrasonic atomizer 10 illustrated in FIGS. 2 to 4 is used to supply a raw material aqueous solution into the atomization tank 11. An organic compound A or a high-concentration aqueous solution is added to the raw material aqueous solution to adjust the concentration of the organic compound A to equal to or greater than 40% by mass, thereby preparing a high-concentration raw material aqueous solution (the initial stage of the concentration adjustment step). Independently of the high-concentration raw material aqueous solution initially supplied into the atomization tank 11, a high-concentration raw material aqueous solution is prepared in such a manner that an aqueous solution containing an organic compound A at a concentration of less than 40% by mass is adjusted to contain the organic compound A at a concentration of equal to or greater than 40% by mass (the concentration adjustment step). While such a high-concentration raw material aqueous solution is being continuously or intermittently supplied through the raw material supply pipe 15, the high-concentration raw material aqueous solution is, in the atomization tank 11, irradiated with an ultrasonic wave by the ultrasonic oscillator 12 to atomize water. As a result, the high-concentration raw material aqueous solution is dehydrated and concentrated (the dehydration concentration step).

Examples of the method for preparing the high-concentration raw material aqueous solution to be supplied to the atomization tank 11 through the raw material supply pipe 15 include the methods of Aspect 2A-(iii)-a, Aspect 2A-(iii)-b, Aspect 2A-(iii)-b', Aspect 2A-(iii)-c, Aspect 2A-(iii)-c', Aspect 2A-(iii)-d, Aspect 2A-(iii)-e, Aspect 2A-(iii)-f, and Aspect 2A-(iii)-g corresponding respectively to Aspect 2A-(i)-a, Aspect 2A-(i)-b, Aspect 2A-(i)-b', Aspect 2A-(i)-c, Aspect 2A-(i)-c', Aspect 2A-(i)-d, Aspect 2A-(i)-e, Aspect 2A-(i)-f, and Aspect 2A-(i)-g.

Aspect 2A-(iv)

In a semi-batch operation (iv) of Aspect 2A, the ultrasonic atomizer 10 illustrated in FIGS. 2 to 4 is used to supply a high-concentration raw material aqueous solution prepared outside the atomization tank 11 into the atomization tank 11 through the raw material supply pipe 15 (the concentration adjustment step). Subsequently, while such a high-concentration raw material aqueous solution is being continuously or intermittently supplied through the raw material supply pipe 15, the high-concentration raw material aqueous solution is, in the atomization tank 11, irradiated with an ultrasonic wave by the ultrasonic oscillator 12 to atomize water. As a result, the high-concentration raw material aqueous solution is dehydrated and concentrated (the dehydration concentration step). Thus, in the semi-batch operation (iv) of Aspect 2A, the high-concentration raw material aqueous solution initially supplied into the atomization tank 11 is the same as the high-concentration aqueous solution supplied at the dehydration concentration step.

Examples of the method for preparing the high-concentration raw material aqueous solution include the methods of Aspect 2A-(iv)-a, Aspect 2A-(iv)-b, Aspect 2A-(iv)-c, Aspect 2A-(iv)-d, Aspect 2A-(iv)-e, and Aspect 2A-(iv)-g corresponding respectively to Aspect 2A-(i)-a, Aspect 2A-(i)-b, Aspect 2A-(i)-c, Aspect 2A-(i)-d, Aspect 2A-(i)-e, and Aspect 2A-(i)-g. In the case where the concentration adjustment step and the dehydration concentration step are performed concurrently with each other, the methods of Aspect 2A-(iv)-b', Aspect 2A-(iv)-c', and Aspect 2A-(iv)-f corresponding respectively to Aspect 2A-(i)-b', Aspect 2A-(i)-c', and Aspect 2A-(i)-f which are the aspects in which the concentrated aqueous solution of the organic compound A formed at the dehydration concentration step is used as the high-concentration aqueous solution to be mixed with the raw material aqueous solution can be employed.

In any of the semi-batch operations (i) to (iv) of Aspect 2A, the concentrated aqueous solution of the organic compound A formed after dehydration concentration may be discharged and recovered through the concentrated aqueous solution discharge pipe 13 extending from the atomization tank 11 (the recovery step).

[Aspect 2B]

In a semi-batch operation of Aspect 2B, the ultrasonic atomizer 10 illustrated in FIG. 2 is used, and an organic compound A or a high-concentration aqueous solution containing an organic compound A at a concentration of greater than 40% by mass is stored in the atomization tank 11. While a raw material aqueous solution stored in the raw material tank 14 and containing an organic compound A at a concentration of less than 40% by mass is being continuously or intermittently supplied through the raw material supply pipe 15 which extends from the raw material tank 14 and which is connected to the atomization tank 11, the raw material aqueous solution and the high-concentration aqueous solution are, in the atomization tank 11, mixed together to prepare a high-concentration raw material aqueous solution adjusted so as to contain the organic compound A at a concentration of equal to or greater than 40% by mass (the concentration adjustment step). Meanwhile, the high-concentration raw material aqueous solution is irradiated with an ultrasonic wave by the ultrasonic oscillator 12 provided in the atomization tank 11 to atomize water. As a result, the high-concentration raw material aqueous solution is dehydrated and concentrated (the dehydration concentration step). At this point, the supply flow rate of the raw material aqueous solution to be supplied is controlled such that the concentration of the organic compound A in the high-concentration raw material aqueous solution in the atomization tank 11 becomes equal to or greater than 40% by mass.

In the semi-batch operation of Aspect 2B, the concentration adjustment step and the dehydration concentration step are performed concurrently with each other in the atomization tank 11. At this point, in the atomization tank 11, the concentration of the organic compound A in the high-concentration raw material aqueous solution increases due to dehydration concentration by ultrasonic wave irradiation. Thus, the concentration of the organic compound A in the high-concentration raw material aqueous solution in the atomization tank 11 can be maintained high in such a manner that the supply flow rate of the raw material aqueous solution to be supplied to the atomization tank 11 through the raw material supply pipe 15 is decreased. The concentration of the high-concentration aqueous solution may be initially adjusted in the atomization tank 11. However, from the viewpoint of shortening of an operation time, it is preferable that an organic compound A or a high-concentration aqueous solution whose concentration is adjusted outside the ultrasonic atomizer 10 is supplied into the atomization tank 11.

In the semi-batch operation of Aspect 2B, the concentrated aqueous solution of the organic compound A formed after dehydration concentration may be discharged and recovered through the concentrated aqueous solution discharge pipe 13 extending from the atomization tank 11 (the recovery step).

<Third Aspect: Continuous Operation>

[Aspect 3A]

Aspect 3A-(i)

In a continuous operation (i) of Aspect 3A, the ultrasonic atomizer 10 illustrated in FIGS. 2 to 4 is used to mix, outside the atomization tank 11, a raw material aqueous solution containing an organic compound A at a concentration of less than 40% by mass with an organic compound A or with a high-concentration aqueous solution containing an organic compound A at a concentration of greater than 40% by mass, thereby preparing a high-concentration raw material aqueous solution adjusted so as to contain the organic compound A at a concentration of equal to or greater than 40% by mass. Alternatively, a raw material aqueous solution is dehydrated and concentrated to prepare a high-concentration raw material aqueous solution adjusted so as to contain an organic compound A at a concentration of equal to or greater than 40% by mass. Then, the high-concentration raw material aqueous solution is directly supplied into the atomization tank 11 of the ultrasonic atomizer 10 (the initial stage of the concentration adjustment step). Examples of the dehydration concentration method for concentration adjustment in the latter case include water atomization by ultrasonic wave irradiation, and moisture evaporation by heating. Then, independently of the high-concentration raw material aqueous solution initially supplied into the atomization tank 11, a high-concentration raw material aqueous solution is prepared in such a manner that an aqueous solution containing an organic compound A at a concentration of less than 40% by mass is adjusted to contain the organic compound A at a concentration of equal to or greater than 40% by mass (the concentration adjustment step). While such a high-concentration raw material aqueous solution is being continuously or intermittently supplied through the raw material supply pipe 15 which extends from the raw material tank 14 and which is connected to the atomization tank 11, the high-concentration raw material aqueous solution is, in the atomization tank 11, irradiated with an ultrasonic wave by the ultrasonic oscillator 12 provided in the atomization tank 11 to atomize water. As a result, the high-concentration raw material aqueous solution is dehydrated and concentrated (the dehydration concentration step). The concentrated aqueous solution of the organic compound A formed after dehydration concentration is continuously or intermittently discharged and recovered through the concentrated aqueous solution discharge pipe 13 extending from the atomization tank 11 (the recovery step).

In the method for preparing the high-concentration raw material aqueous solution to be supplied to the atomization tank 11 through the raw material supply pipe 15, a raw material aqueous solution may be, outside the raw material tank 14, mixed with an organic compound A or with a high-concentration aqueous solution, thereby preparing a high-concentration raw material aqueous solution adjusted so as to contain the organic compound A at a concentration of equal to or greater than 40% by mass. Alternatively, a raw material aqueous solution may be dehydrated and concentrated, thereby preparing a high-concentration raw material aqueous solution adjusted so as to contain an organic compound A at a concentration of equal to or greater than 40% by mass. Then, the high-concentration raw material aqueous solution may be supplied into the raw material tank 14 and stored in the raw material tank 14 (Aspect 3A-(i)-a). The concentration adjustment step of the high-concentration raw material aqueous solution in Aspect 3A-(i)-a may be performed concurrently with the dehydration concentration step. In such a case, part or all of the high-concentration aqueous solution to be mixed with the raw material aqueous solution may be, in the former method, the concentrated aqueous solution of the organic compound A formed at the dehydration concentration step. Examples of the latter dehydration concentration method for concentration adjustment include water atomization by ultrasonic wave irradiation, and moisture evaporation by heating. The high-concentration raw material aqueous solution supplied into the raw material tank 14 may be the same as the high-concentration raw material aqueous solution initially supplied into the atomization tank 11.

An organic compound A or a high-concentration aqueous solution may be supplied into the raw material tank 14, and then a raw material aqueous solution is added to the organic compound A or the high-concentration aqueous solution to prepare a high-concentration raw material aqueous solution adjusted so as to contain the organic compound A at a concentration of equal to or greater than 40% by mass (Aspect 3A-(i)-b). The concentration adjustment step of the high-concentration raw material aqueous solution in Aspect 3A-(i)-b may be performed concurrently with the dehydration concentration step. In such a case, part or all of the high-concentration aqueous solution to be mixed with the raw material aqueous solution may be the concentrated aqueous solution of the organic compound A formed at the dehydration concentration step. For example, the ultrasonic atomizer 10 illustrated in FIG. 3 may be used to supply the concentrated aqueous solution of the organic compound A formed at the dehydration concentration step to the raw material tank 14 through the return pipe 16 which branches from the concentrated aqueous solution discharge pipe 13 and which is connected to the raw material tank 14, and therefore part or all of the high-concentration aqueous solution supplied into the raw material tank 14 may be the concentrated aqueous solution of the organic compound A (Aspect 3A-(i)-b').

A raw material aqueous solution may be supplied into the raw material tank 14, and then an organic compound A or a high-concentration aqueous solution is added to the raw material aqueous solution to prepare a high-concentration raw material aqueous solution adjusted so as to contain the organic compound A at a concentration of equal to or greater than 40% by mass (Aspect 3A-(i)-c). The concentration adjustment step of the high-concentration raw material aqueous solution in Aspect 3A-(i)-c may be performed concurrently with the dehydration concentration step. In such a case, part or all of the high-concentration aqueous solution to be mixed with the raw material aqueous solution may be the concentrated aqueous solution of the organic compound A formed at the dehydration concentration step. For example, the ultrasonic atomizer 10 illustrated in FIG. 3 may be used to supply the concentrated aqueous solution of the organic compound A formed at the dehydration concentration step to the raw material tank 14 through the return pipe 16 which branches from the concentrated aqueous solution discharge pipe 13 and which is connected to the raw material tank 14, and therefore part or all of the high-concentration aqueous solution to be added to the raw material aqueous solution supplied into the raw material tank 14 may be the concentrated aqueous solution of the organic compound A (Aspect 3A-(i)-c').

A raw material aqueous solution may be supplied into the raw material tank 14, and may be dehydrated and concentrated to prepare a high-concentration raw material aqueous solution adjusted so as to contain an organic compound A at a concentration of equal to or greater than 40% by mass (Aspect 3A-(i)-d). Examples of the dehydration concentration method for concentration adjustment include water atomization by ultrasonic wave irradiation, and moisture evaporation by heating.

Such a high-concentration raw material aqueous solution may be prepared in the course of supplying the raw material aqueous solution from the raw material tank 14 to the atomization tank 11 through the raw material supply pipe 15.

For example, the ultrasonic atomizer 10 illustrated in FIG. 4A may be used to supply a raw material aqueous solution into the raw material tank 14. In the course of supplying the raw material aqueous solution to the atomization tank 11 through the raw material supply pipe 15, an organic compound A or a high-concentration aqueous solution may join the raw material aqueous solution through the organic-compound-A supply pipe 17 connected to the raw material supply pipe 15, and therefore a high-concentration raw material aqueous solution adjusted so as to contain the organic compound A at a concentration of equal to or greater than 40% by mass may be prepared (Aspect 3A-(i)-e). The concentration adjustment step of the high-concentration raw material aqueous solution in Aspect 3A-(i)-e is performed concurrently with the dehydration concentration step.

The ultrasonic atomizer 10 illustrated in FIG. 4B may be used to supply a raw material aqueous solution into the raw material tank 14. In the course of supplying the raw material aqueous solution to the atomization tank 11 through the raw material supply pipe 15, the concentrated aqueous solution of the organic compound A formed at the dehydration concentration step may join the raw material aqueous solution through the return pipe 18 which branches from the concentrated aqueous solution discharge pipe 13 and which is connected to the raw material supply pipe 15, and therefore a high-concentration raw material aqueous solution adjusted so as to contain the organic compound A at a concentration of equal to or greater than 40% by mass may be prepared (Aspect 3A-f). The concentration adjustment step of the high-concentration raw material aqueous solution in Aspect 3A-(i)-f is performed concurrently with the dehydration concentration step. Moreover, the concentrated aqueous solution of the organic compound A formed at the dehydration concentration step is used as the high-concentration aqueous solution to be mixed with the raw material aqueous solution.

The ultrasonic atomizer 10 illustrated in FIG. 4C may be used to supply a raw material aqueous solution into the raw material tank 14. In the course of supplying the raw material aqueous solution to the atomization tank 11 through the raw material supply pipe 15, a high-concentration raw material aqueous solution adjusted so as to contain an organic compound A at a concentration of equal to or greater than 40% by mass may be prepared in the concentration adjuster 19 provided in the raw material supply pipe 15 (Aspect 3A-(i)-g). The concentration adjustment step of the high-concentration raw material aqueous solution in Aspect 3A-(i)-g is performed concurrently with the dehydration concentration step. Moreover, in the concentration adjuster 19, the concentrated aqueous solution of the organic compound A formed at the dehydration concentration step may be used to perform concentration adjustment.

The concentration adjuster 19 may be an atomization tank in which a raw material aqueous solution is dehydrated and concentrated by ultrasonic atomization. In such a case, atomization tanks each provided with an ultrasonic oscillator are continuously provided. The concentration of a raw material aqueous solution is adjusted in the upstream atomization tank serving as the concentration adjuster 19, and the high-concentration raw material aqueous solution whose concentration is adjusted is dehydrated and concentrated in the downstream atomization tank 11. The concentration adjuster 19 may be a unit other than the dehydration concentration unit using ultrasonic atomization, such as a heating tank capable of evaporating moisture of a raw material aqueous solution by heating to dehydrate and concentrate the raw material aqueous solution.

Aspect 3A-(ii)

In a continuous operation (ii) of Aspect 3A, the ultrasonic atomizer 10 illustrated in FIGS. 2 to 4 is used to supply an organic compound A or a high-concentration aqueous solution into the atomization tank 11. A raw material aqueous solution is added to the organic compound A or the high-concentration aqueous solution to prepare a high-concentration raw material aqueous solution adjusted so as to contain the organic compound A at a concentration of equal to or greater than 40% by mass (the initial stage of the concentration adjustment step). Independently of the high-concentration raw material aqueous solution initially supplied into the atomization tank 11, a high-concentration raw material aqueous solution is prepared in such a manner that an aqueous solution containing an organic compound A at a concentration of less than 40% by mass is adjusted to contain the organic compound A at a concentration of equal to or greater than 40% by mass (the concentration adjustment step). While such a high-concentration raw material aqueous solution is being continuously or intermittently supplied through the raw material supply pipe 15, the high-concentration raw material aqueous solution is, in the atomization tank 11, irradiated with an ultrasonic wave by the ultrasonic oscillator 12 to atomize water. As a result, the high-concentration raw material aqueous solution is dehydrated and concentrated (the dehydration concentration step). The concentrated aqueous solution of the organic compound A formed after dehydration concentration is continuously or intermittently discharged and recovered through the concentrated aqueous solution discharge pipe 13 (the recovery step).

Examples of the method for preparing the high-concentration raw material aqueous solution to be supplied to the atomization tank 11 through the raw material supply pipe 15 include the methods of Aspect 3A-(ii)-a, Aspect 3A-(ii)-b, Aspect 3A-(ii)-b', Aspect 3A-(ii)-c, Aspect 3A-(ii)-c', Aspect 3A-(ii)-d, Aspect 3A-(ii)-e, Aspect 3A-(ii)-f, and Aspect 3A-(ii)-g corresponding respectively to Aspect 3A-(i)-a, Aspect 3A-(i)-b, Aspect 3A-(i)-b', Aspect 3A-(i)-c, Aspect 3A-(i)-c', Aspect 3A-(i)-d, Aspect 3A-(i)-e, Aspect 3A-(i)-f, and Aspect 3A-(i)-g.

Aspect 3A-(iii)

In a continuous operation (iii) of Aspect 3A, the ultrasonic atomizer 10 illustrated in FIGS. 2 to 4 is used to supply a raw material aqueous solution into the atomization tank 11. An organic compound A or a high-concentration aqueous solution is added to the raw material aqueous solution to adjust the concentration of the organic compound A to equal to or greater than 40% by mass, thereby preparing a high-concentration raw material aqueous solution (the initial stage of the concentration adjustment step). Independently of the high-concentration raw material aqueous solution initially supplied into the atomization tank 11, a high-concentration raw material aqueous solution is prepared in such a manner that an aqueous solution containing an organic compound A at a concentration of less than 40% by mass is adjusted to contain the organic compound A at a concentration of equal to or greater than 40% by mass (the concentration adjustment step). While such a high-concentration raw material aqueous solution is being continuously or intermittently supplied through the raw material supply pipe 15, the high-concentration raw material aqueous solution is, in the atomization tank 11, irradiated with an ultrasonic wave by the ultrasonic oscillator 12 to atomize water. As a result, the high-concentration raw material aqueous solution is dehydrated and concentrated (the dehydration concentration step). The concentrated aqueous solution of the organic compound A formed after dehydration concentration is continuously or intermittently discharged and recovered through the concentrated aqueous solution discharge pipe 13 (the recovery step).

Examples of the method for preparing the high-concentration raw material aqueous solution to be supplied to the atomization tank 11 through the raw material supply pipe 15 include the methods of Aspect 3A-(iii)-a, Aspect 3A-(iii)-b, Aspect 3A-(iii)-b', Aspect 3A-(iii)-c, Aspect 3A-(iii)-c', Aspect 3A-(iii)-d, Aspect 3A-(iii)-e, Aspect 3A-(iii)-f, and Aspect 3A-(iii)-g corresponding respectively to Aspect 3A-(i)-a, Aspect 3A-(i)-b, Aspect 3A-(i)-b', Aspect 3A-(i)-c, Aspect 3A-(i)-c', Aspect 3A-(i)-d, Aspect 3A-(i)-e, Aspect 3A-(i)-f, and Aspect 3A-(i)-g.

Aspect 3A-(iv)

In a continuous operation (iv) of Aspect 3A, the ultrasonic atomizer 10 illustrated in FIGS. 2 to 4 is used to supply a high-concentration raw material aqueous solution prepared outside the atomization tank 11 into the atomization tank 11 through the raw material supply pipe 15 (the concentration adjustment step). Subsequently, while such a high-concentration raw material aqueous solution is being continuously or intermittently supplied through the raw material supply pipe 15, the high-concentration raw material aqueous solution is, in the atomization tank 11, irradiated with an ultrasonic wave by the ultrasonic oscillator 12 to atomize water. As a result, the high-concentration raw material aqueous solution is dehydrated and concentrated (the dehydration concentration step). Thus, in the continuous operation (iv) of Aspect 3A, the high-concentration raw material aqueous solution initially supplied into the atomization tank 11 is the same as the high-concentration aqueous solution supplied at the dehydration concentration step. The concentrated aqueous solution of the organic compound A formed after dehydration concentration is continuously or intermittently discharged and recovered through the concentrated aqueous solution discharge pipe 13 (the recovery step).

Examples of the method for preparing the high-concentration raw material aqueous solution include the methods of Aspect 3A-(iv)-a, Aspect 3A-(iv)-b, Aspect 3A-(iv)-c, Aspect 3A-(iv)-d, Aspect 3A-(iv)-e, and Aspect 3A-(iv)-g corresponding respectively to Aspect 3A-(i)-a, Aspect 3A-(i)-b, Aspect 3A-(i)-c, Aspect 3A-(i)-d, Aspect 3A-(i)-e, and Aspect 3A-(i)-g. In the case where the concentration adjustment step and the dehydration concentration step are performed concurrently with each other in a steady state, the methods of Aspect 3A-(iv)-b', Aspect 3A-(iv)-c', and Aspect 3A-(iv)-f corresponding respectively to Aspect 3A-(i)-b', Aspect 3A-(i)-c', and Aspect 3A-(i)-f which are the aspects in which the concentrated aqueous solution of the organic compound A formed at the dehydration concentration step is used as the high-concentration aqueous solution to be mixed with the raw material aqueous solution can be employed.

[Aspect 3B]

In a continuous operation of Aspect 3B, the ultrasonic atomizer 10 illustrated in FIG. 2 is used, and an organic compound A or a high-concentration aqueous solution containing an organic compound A at a concentration of greater than 40% by mass is stored in the atomization tank 11. While a raw material aqueous solution stored in the raw material tank 14 and containing an organic compound A at a concentration of less than 40% by mass is being continuously or intermittently supplied through the raw material supply pipe 15 which extends from the raw material tank 14 and which is connected to the atomization tank 11, the raw material aqueous solution and the high-concentration aqueous solution are, in the atomization tank 11, mixed together to prepare a high-concentration raw material aqueous solution adjusted so as to contain the organic compound A at a concentration of equal to or greater than 40% by mass (the concentration adjustment step). Meanwhile, the high-concentration raw material aqueous solution is irradiated with an ultrasonic wave by the ultrasonic oscillator 12 provided in the atomization tank 11 to atomize water. As a result, the high-concentration raw material aqueous solution is dehydrated and concentrated (the dehydration concentration step). The concentrated aqueous solution of the organic compound A formed after dehydration concentration is continuously or intermittently discharged and recovered through the concentrated aqueous solution discharge pipe 13 extending from the atomization tank 11 (the recovery step). At this point, the supply flow rate of the raw material aqueous solution to be supplied and the recovery flow rate of the concentrated aqueous solution to be recovered are controlled such that the concentration of the organic compound A in the high-concentration raw material aqueous solution in the atomization tank 11 becomes equal to or greater than 40% by mass.

In the continuous operation of Aspect 3B, the concentration adjustment step and the dehydration concentration step are performed concurrently with each other in the atomization tank 11. At this point, in the atomization tank 11, the concentration of the organic compound A in the high-concentration raw material aqueous solution increases due to dehydration concentration by ultrasonic wave irradiation. Thus, the concentration of the organic compound A in the high-concentration raw material aqueous solution in the atomization tank 11 can be maintained high in such a manner that the supply flow rate of the raw material aqueous solution to be supplied to the atomization tank 11 through the raw material supply pipe 15 is decreased. The concentration of the high-concentration aqueous solution may be initially adjusted in the atomization tank 11. However, from the viewpoint of shortening of an operation time, it is preferable that an organic compound A or a high-concentration aqueous solution whose concentration is adjusted outside the ultrasonic atomizer 10 is supplied into the atomization tank 11.

Regarding the foregoing embodiment, the concentrated aqueous solution producing method and the concentration step thereof will be further described as follows.

<1> The method for producing a concentrated aqueous solution of an organic compound, including a concentration adjustment step of adjusting an aqueous solution containing the organic compound at a concentration of less than 40% by mass to contain the organic compound at a concentration of equal to or greater than 40% by mass, the organic compound having two or more hydrophilic groups in a molecule; and a dehydration concentration step of irradiating the aqueous solution whose organic compound concentration is adjusted to equal to or greater than 40% by mass at the concentration adjustment step with an ultrasonic wave to atomize water.

<2> The method of <1>, in which the concentration of the organic compound in the raw material aqueous solution is preferably equal to or less than 35% by mass, more preferably equal to or less than 30% by mass, much more preferably equal to or less than 25% by mass, and still much more preferably equal to or less than 20% by mass, and is equal to or greater than 0.1% by mass, preferably equal to or greater than 0.5% by mass, more preferably equal to or greater than 1% by mass, much more preferably equal to or greater than 3% by mass, and still much more preferably equal to or greater than 5% by mass.

<3> The method of <1> or <2>, in which the concentration of the organic compound in the aqueous solution whose concentration is adjusted at the concentration adjustment step is preferably equal to or greater than 45% by mass, more preferably equal to or greater than 50% by mass, and much more preferably equal to or greater than 60% by mass, and is equal to or less than 99% by mass, preferably equal to or less than 95% by mass, more preferably equal to or less than 90% by mass, much more preferably equal to or less than 80% by mass, and still much more preferably equal to or less than 70% by mass.

<4> The method of any one of <1> to <3>, in which concentration adjustment at the concentration adjustment step is performed in such a manner that the aqueous solution containing the organic compound at a concentration of less than 40% by mass is mixed with the organic compound or an aqueous solution containing the organic compound at a concentration of greater than 40% by mass, and the aqueous solution containing the organic compound at a concentration of less than 40% by mass is mixed with the organic compound or the aqueous solution containing the organic compound at a concentration of greater than 40% by mass, preferably equal to or greater than 45% by mass, more preferably equal to or greater than 50% by mass, and much more preferably equal to or greater than 60% by mass and at a concentration of equal to or less than 99% by mass, preferably equal to or less than 95% by mass, more preferably equal to or less than 90% by mass, much more preferably equal to or less than 80% by mass, and still much more preferably equal to or less than 70% by mass.

<5> The method of any one of <1> to <4>, which further includes a recovery step of recovering the concentrated aqueous solution of the organic compound formed by dehydration concentration at the dehydration concentration step.

<6> The method of any one of <1> to <5>, in which the concentration adjustment at the concentration adjustment step is performed in an ultrasonic atomizer including an atomization tank provided with an ultrasonic oscillator.

<7> The method of any one of <1> to <6>, in which, at the concentration adjustment step, the aqueous solution whose organic compound concentration is adjusted to equal to or greater than 40% by mass is supplied into the atomization tank provided with the ultrasonic oscillator.

<8> The method of any one of <1> to <7>, in which the concentrated aqueous solution of the organic compound is produced by a batch operation.

<9> The method of any one of <1> to <7>, in which the concentrated aqueous solution of the organic compound is produced by a semi-batch operation in which the aqueous solution formed, at the concentration adjustment step, in such a manner that the aqueous solution containing the organic compound at a concentration of less than 40% by mass is adjusted to contain the organic compound at a concentration of equal to or greater than 40% by mass is continuously or intermittently supplied to the aqueous solution of the organic compound which is to be dehydrated and concentrated at the dehydration concentration step.

<10> The method of any one of <1> to <7>, in which the concentrated aqueous solution of the organic compound is produced by a continuous operation in which the aqueous solution formed, at the concentration adjustment step, in such a manner that the aqueous solution containing the organic compound at a concentration of less than 40% by mass is adjusted to contain the organic compound at a concentration of equal to or greater than 40% by mass is continuously or intermittently supplied to the aqueous solution of the organic compound which is to be dehydrated and concentrated at the dehydration concentration step, and the concentrated aqueous solution of the organic compound is continuously or intermittently recovered.

<11> The method of <9> or <10>, in which the concentration adjustment of the concentration adjustment step for the aqueous solution to be continuously or intermittently supplied to the aqueous solution of the organic compound which is to be dehydrated and concentrated at the dehydration concentration step is performed concurrently with the dehydration concentration step in such a manner that the aqueous solution containing the organic compound at a concentration of less than 40% by mass is mixed with the aqueous solution containing the organic compound at a concentration of greater than 40% by mass, preferably equal to or greater than 45% by mass, more preferably equal to or greater than 50% by mass, and much more preferably equal to or greater than 60% by mass and at a concentration of equal to or less than 99% by mass, preferably equal to or less than 95% by mass, more preferably equal to or less than 90% by mass, much more preferably equal to or less than 80% by mass, and still much more preferably equal to or less than 70% by mass.

<12> The method of <11>, in which part or all of the aqueous solution containing the organic compound at a concentration of greater than 40% by mass is the concentrated aqueous solution of the organic compound formed by dehydration concentration at the dehydration concentration step.

<13> The method of any one of <1> to <7>, in which the concentrated aqueous solution of the organic compound is produced by a semi-batch operation in which, while the aqueous solution containing the organic compound at a concentration of less than 40% by mass is continuously or intermittently supplied to the aqueous solution of the organic compound which is to be dehydrated and concentrated at the dehydration concentration step, the concentration adjustment step is performed in such a manner that the supply flow rate of the aqueous solution containing the organic compound at a concentration of less than 40% by mass is controlled such that the aqueous solution of the organic compound which is to be dehydrated and concentrated contains the organic compound at a concentration of equal to or greater than 40% by mass.

<14> The method of any one of <1> to <7>, in which the concentrated aqueous solution of the organic compound is produced by a continuous operation in which, while the aqueous solution containing the organic compound at a concentration of less than 40% by mass is continuously or intermittently supplied to the aqueous solution of the organic compound which is to be dehydrated and concentrated at the dehydration concentration step, and the concentrated aqueous solution of the organic compound formed by dehydration concentration at the dehydration concentration step is continuously or intermittently recovered, the concentration adjustment step is performed in such a manner that the supply flow rate of the aqueous solution containing the organic compound at a concentration of less than 40% by mass and the recovery flow rate of the concentrated aqueous solution are controlled such that the aqueous solution of the organic compound which is to be dehydrated and concentrated contains the organic compound at the concentration of equal to or greater than 40% by mass.

<15> The method of any one of <1> to <14>, in which, at the dehydration concentration step, the concentration of the organic compound in the aqueous solution in ultrasonic wave irradiation is preferably equal to or greater than 40% by mass, more preferably equal to or greater than 45% by mass, much more preferably equal to or greater than 50% by mass, and still much more preferably equal to or greater than 60% by mass, and is preferably equal to or less than 99% by mass, more preferably equal to or less than 90% by mass, much more preferably equal to or less than 80% by mass, and still much more preferably equal to or less than 70% by mass.

<16> The method of any one of <1> to <15>, in which, at the dehydration concentration step, the concentration of the organic compound in liquid drops atomized is equal to or less than 5% by mass, preferably equal to or less than 3% by mass, more preferably equal to or less than 1% by mass, much more preferably equal to or less than 0.5% by mass, and still much more preferably equal to or less than 0.25% by mass.

<17> The method of any one of <1> to <16>, in which, at the dehydration concentration step, the viscosity of the aqueous solution in ultrasonic wave irradiation is preferably equal to or less than 25 mPa·s, more preferably equal to or less than 20 mPa·s, and much more preferably equal to or less than 15 mPa·s.

<18> The method of any one of <1> to <17>, in which, at the dehydration concentration step, the concentration of the organic compound in the concentrated aqueous solution after dehydration concentration is preferably equal to or greater than 40% by mass, more preferably equal to or greater than 45% by mass, much more preferably equal to or greater than 50% by mass, and still much more preferably equal to or greater than 60% by mass, and is preferably equal to or less than 100% by mass, more preferably equal to or less than 98% by mass, and much more preferably equal to or less than 95% by mass.

<19> The method of any one of <1> to <18>, in which, at the dehydration concentration step, the viscosity of the concentrated aqueous solution of the organic compound after dehydration concentration is preferably equal to or less than 25 mPa·s, more preferably equal to or less than 20 mPa·s, and much more preferably 15 mPa·s.

<20> The method of any one of <1> to <19>, in which the temperature of the aqueous solution irradiated with the ultrasonic wave at the dehydration concentration step is preferably equal to or higher than 10° C., more preferably equal to or higher than 20° C., much more preferably equal to or higher than 30° C., and still much more preferably equal to or higher than 40° C., and is preferably equal to or lower than 100° C., more preferably equal to or lower than 90° C., much more preferably equal to or lower than 80° C., still much more preferably equal to or lower than 70° C.

<21> The method of <20>, in which the temperature of the aqueous solution irradiated with the ultrasonic wave at the dehydration concentration step is equal to or higher than 50° C. and equal to or lower than 100° C.

<22> The method of any one of <1> to <21>, in which the frequency of ultrasonic vibrations applied to the aqueous solution at the dehydration concentration step is preferably equal to or higher than 20 kHz, and more preferably equal to or higher than 1 MHz, and is preferably equal to or lower than 10 MHz, and more preferably equal to or lower than 5 MHz.

<23> The method of any one of <1> to <22>, in which the organic compound has, as the hydrophilic groups, one or more chosen from the group consisting of a hydroxyl group, a carboxyl group, a carbonyl group, an ester group, an acetal group, a hemiacetal group, an ether group, an amino group, an ammonium group, an amide group, a sulfonate group, a sulfate ester group, a phosphonate group, a phosphate group, or an ureido group, preferably has one or more chosen from the group consisting of a hydroxyl group, a carboxyl group, a carbonyl group, an acetal group, a hemiacetal group, an amino group, an ammonium group, a sulfonate group, a sulfate ester group, a phosphonate group, or a phosphate group, more preferably has one or more chosen from the group consisting of a hydroxyl group, a carboxyl group, a carbonyl group, an acetal group, a hemiacetal group, an amino group, or a sulfonate group, and much more preferably has one or more chosen from the group consisting of a hydroxyl group or a carboxyl group <24> The method of <23>, in which the organic compound contains polyhydric alcohol.

<25> The method of <24>, in which the polyhydric alcohol which is the organic compound is one or more chosen from the group consisting of diols each having two hydroxyl groups in a molecule, triols each having three hydroxyl groups in a molecule, tetraols each having four hydroxyl groups in a molecule, or sugars.

<26> The method of any one of <23> to <25>, in which the organic compound contains an organic compound having a carboxyl group.

<27> The method of <26>, in which the organic compound having the carboxyl group is one or more chosen from the group consisting of polyhydric carboxylic acid having two or more carboxyl groups in a molecule, hydroxy acid having a hydroxyl group and a carboxyl group in a molecule, or amino acid having a carboxyl group and an amino group in a molecule.

<28> The method of any one of <1> to <27>, in which the molecule of the organic compound has preferably equal to or greater than two carbon atoms and more preferably equal to or greater than three carbon atoms, and has preferably equal to or less than 22 carbon atoms, more preferably equal to or less than 12 carbon atoms, and much more preferably six carbon atoms.

<29> The method of any one of <1> to <28>, in which the molecular weight of the organic compound is preferably equal to or greater than 50, more preferably equal to or greater than 60, and much more preferably equal to or greater than 70, and is preferably equal to or less than 400, equal to or less than 300, and equal to or less than 200.

<30> The method of any one of <1> to <29>, in which the number of hydrophilic groups in the molecule of the organic compound is preferably equal to or less than 10, more preferably equal to or less than eight, much more preferably equal to or less than five, and still much more preferably equal to or less than three.

<31> The method of any one of <1> to <30>, in which the organic compound is an organic compound in which a plurality of hydrophilic groups are bonded to the same carbon atom, or an organic compound in which a plurality of hydrophilic groups are bonded respectively to adjacent carbon atoms.

<32> The method of any one of <1> to <31>, in which the degree of solubility of the organic compound in a water of 100 g at 25° C. is preferably equal to or greater than 67 g, more preferably equal to or greater than 100 g, and much more preferably equal to or greater than 150 g.

<33> A dehydration concentration method including the step of adjusting an aqueous solution containing an organic compound at a concentration of less than 40% by mass to contain the organic compound at a concentration of equal to or greater than 40% by mass, the organic compound having two or more hydrophilic groups in a molecule; and the step of irradiating the aqueous solution whose organic compound concentration is adjusted to equal to or greater than 40% by mass with an ultrasonic wave to atomize water.

EXAMPLES (Analysis Method)

[Measurement Conditions for High Performance Liquid Chromatography (HPLC)]

The concentration of an organic compound in a sampled organic compound aqueous solution was measured using HPLC. The analysis conditions for HPLC were as follows:

Device Name: LaChrom Elite (manufactured by Hitachi High-Technologies Corporation);

Column: ICSep ICE-ION-300;

Eluent: 0.0085 N Sulfric Acid at 0.4 mL/min;

Detector: RI (L-2490 manufactured by Hitachi High-Technologies Corporation);

Column Temperature: 40° C.;

Amount of Liquid to be Supplied: 20 μL; and

Holding Time: 40 min.

(Ultrasonic Atomizer for Experiment)

FIG. 5 illustrates an experimental ultrasonic atomizer 20 used for the following experiment.

The experimental ultrasonic atomizer 20 includes an atomization tank 21 provided with a temperature control mechanism. An ultrasonic oscillator 22 (having an oscillation frequency of 2.4 MHz and an output of 30 W) is provided in the atomization tank 21. A raw material supply pipe 25 extending from a raw material tank 24 is joined to a lower part of the atomization tank 21. A return pipe 26 provided with a liquid supply pump which is not shown in the figure extends from the lower part of the atomization tank 21, and is joined to the raw material tank 24. Thus, an aqueous solution circulates between the raw material tank 24 and the atomization tank 21 through the raw material supply pipe 25 and the return pipe 26. A carrier gas supply pipe 27 extending from a gas source which is not shown in the figure is joined to an upper part of the atomization tank 21. A mist collecting pipe 28 extends from a top part of the atomization tank 21, and is joined to a mist collector 29.

First Experiment

First Example

Glycerol (the number of carbon atoms: 3, the molecular weight: 92, and the number of hydrophilic groups: 3) was added to a glycerol aqueous solution containing glycerol at a concentration of 20.7% by mass to adjust the glycerol concentration of the resultant to 48% by mass. Then, a glycerol aqueous solution, whose concentration is adjusted to 48% by mass, of 841 g was supplied into the raw material tank 24 of the experimental ultrasonic atomizer 20. While the glycerol aqueous solution whose temperature is controlled to 60° C. was circulating between the raw material tank 24 and the atomization tank 21 through the raw material supply pipe 25 and the return pipe 26, dehydration concentration by ultrasonic wave irradiation was performed for 9.0 hours in the batch operation. Then, the amount of liquid drops collected by the mist collector 29, the glycerol concentration in the liquid drops, and the glycerol concentration in the dehydrated and concentrated aqueous solution in the atomization tank 21 were measured.

Second Example

Glycerol was added to a glycerol aqueous solution containing glycerol at a concentration of 10.1% by mass to adjust the glycerol concentration of the resultant to 59% by mass. Then, a glycerol aqueous solution, whose concentration is adjusted to 59% by mass, of 804 g was supplied into the raw material tank 24 of the experimental ultrasonic atomizer 20. While the glycerol aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 2.5 hours in the batch operation. Then, as in the first example, the amount of liquid drops collected by the mist collector 29, the glycerol concentration in the liquid drops, and the glycerol concentration in the dehydrated and concentrated aqueous solution in the atomization tank 21 were measured.

Third Example

Lactic acid (the number of carbon atoms: 3, the molecular weight: 90, and the number of hydrophilic groups: 2) was added to a lactic acid aqueous solution containing lactic acid at a concentration of 5.00% by mass to adjust the lactic acid concentration of the resultant to 44% by mass. Then, a lactic acid aqueous solution, whose concentration is adjusted to 44% by mass, of 805 g was supplied into the raw material tank 24 of the experimental ultrasonic atomizer 20. While the lactic acid aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 6.0 hours in the batch operation. Then, as in the first example, the amount of liquid drops collected by the mist collector 29, the lactic acid concentration in the liquid drops, and the lactic acid concentration in the dehydrated and concentrated aqueous solution in the atomization tank 21 were measured.

Fourth Example

Glucose (the number of carbon atoms: 6, the molecular weight: 180, and the number of hydrophilic groups: 5) was added to a glucose aqueous solution containing glucose at a concentration of 5.00% by mass to adjust the glucose concentration of the resultant to 62% by mass. Then, a glucose aqueous solution, whose concentration is adjusted to 62% by mass, of 800 g was supplied into the raw material tank 24 of the experimental ultrasonic atomizer 20. While the glucose aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 1.0 hour in the batch operation. Then, as in the first example, the amount of liquid drops collected by the mist collector 29, the glucose concentration in the liquid drops, and the glucose concentration in the dehydrated and concentrated aqueous solution in the atomization tank 21 were measured.

Fifth Example

First, 1,2-propanediol (the number of carbon atoms: 3, the molecular weight: 76, and the number of hydrophilic groups: 2) was added to a 1,2-propanediol aqueous solution containing 1,2-propanediol at a concentration of 5.00% by mass to adjust the 1,2-propanediol concentration of the resultant to 51% by mass. Then, a 1,2-propanediol aqueous solution, whose concentration is adjusted to 51% by mass, of 504 g was supplied into the raw material tank 24 of the experimental ultrasonic atomizer 20. While the 1,2-propanediol aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 0.5 hour in the batch operation. Then, as in the first example, the amount of liquid drops collected by the mist collector 29, the 1,2-propanediol concentration in the liquid drops, and the 1,2-propanediol concentration in the dehydrated and concentrated aqueous solution in the atomization tank 21 were measured.

Sixth Example

Xylose (the number of carbon atoms: 5, the molecular weight: 150, and the number of hydrophilic groups: 4) was added to a xylose aqueous solution containing xylose at a concentration of 5.00% by mass to adjust the xylose concentration of the resultant to 42% by mass. Then, a xylose aqueous solution, whose concentration is adjusted to 42% by mass, of 801 g was supplied into the raw material tank 24 of the experimental ultrasonic atomizer 20. While the xylose aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 0.4 hour in the batch operation. Then, as in the first example, the amount of liquid drops collected by the mist collector 29, the xylose concentration in the liquid drops, and the xylose concentration in the dehydrated and concentrated aqueous solution in the atomization tank 21 were measured.

Seventh Example

Hydroxymethylfurfural (the number of carbon atoms: 6, the molecular weight: 126, and the number of hydrophilic groups: 3) was added to a hydroxymethylfurfural aqueous solution containing hydroxymethylfurfural at a concentration of 5.00% by mass to adjust the hydroxymethylfurfural concentration of the resultant to 51% by mass. Then, a hydroxymethylfurfural aqueous solution, whose concentration is adjusted to 51% by mass, of 600 g was supplied into the raw material tank 24 of the experimental ultrasonic atomizer 20. While the hydroxymethylfurfural aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 1.5 hours in the batch operation. Then, as in the first example, the amount of liquid drops collected by the mist collector 29, the hydroxymethylfurfural concentration in the liquid drops, and the hydroxymethylfurfural concentration in the dehydrated and concentrated aqueous solution in the atomization tank 21 were measured.

First Comparative Example

A glycerol aqueous solution, which contains glycerol at a concentration of 22% by mass, of 801 g was supplied into the raw material tank 24 of the experimental ultrasonic atomizer 20. While the glycerol aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 2.3 hours in the batch operation. Then, as in the first example, the amount of liquid drops collected by the mist collector 29, the glycerol concentration in the liquid drops, and the glycerol concentration in the dehydrated and concentrated aqueous solution in the atomization tank 21 were measured.

Second Comparative Example

A lactic acid aqueous solution, which contains lactic acid at a concentration of 4.8% by mass, of 857 g was supplied into the raw material tank 24 of the experimental ultrasonic atomizer 20. While the lactic acid aqueous solution whose temperature is controlled to 70° C. was circulating between the raw material tank 24 and the atomization tank 21 through the raw material supply pipe 25 and the return pipe 26, dehydration concentration by ultrasonic wave irradiation was performed for 1.7 hours in the batch operation. Then, as in the first example, the amount of liquid drops collected by the mist collector 29, the lactic acid concentration in the liquid drops, and the lactic acid concentration in the dehydrated and concentrated aqueous solution in the atomization tank 21 were measured.

Third Comparative Example

A lactic acid aqueous solution, which contains lactic acid at a concentration of 20% by mass, of 701 g was supplied into the raw material tank 24 of the experimental ultrasonic atomizer 20. While the lactic acid aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 2.0 hours in the batch operation. Then, as in the first example, the amount of liquid drops collected by the mist collector 29, the lactic acid concentration in the liquid drops, and the lactic acid concentration in the dehydrated and concentrated aqueous solution in the atomization tank 21 were measured.

Fourth Comparative Example

A glucose aqueous solution, which contains glucose at a concentration of 20% by mass, of 801 g was supplied into the raw material tank 24 of the experimental ultrasonic atomizer 20. While the glucose aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 0.9 hour in the batch operation. Then, as in the first example, the amount of liquid drops collected by the mist collector 29, the glucose concentration in the liquid drops, and the glucose concentration in the dehydrated and concentrated aqueous solution in the atomization tank 21 were measured.

Fifth Comparative Example

A glycerol aqueous solution, which contains glycerol at a concentration of 30% by mass, of 801 g was supplied into the raw material tank 24 of the experimental ultrasonic atomizer 20. While the glycerol aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 0.3 hour in the batch operation. Then, as in the first example, the amount of liquid drops collected by the mist collector 29, the glycerol concentration in the liquid drops, and the glycerol concentration in the dehydrated and concentrated aqueous solution in the atomization tank 21 were measured.

Sixth Comparative Example

A 1,2-propanediol aqueous solution, which contains 1,2-propanediol at a concentration of 31% by mass, of 402 g was supplied into the raw material tank 24 of the experimental ultrasonic atomizer 20. While the 1,2-propanediol aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 0.4 hour in the batch operation. Then, as in the first example, the amount of liquid drops collected by the mist collector 29, the 1,2-propanediol concentration in the liquid drops, and the 1,2-propanediol concentration in the dehydrated and concentrated aqueous solution in the atomization tank 21 were measured.

Seventh Comparative Example

A xylose aqueous solution, which contains xylose at a concentration of 30% by mass, of 802 g was supplied into the raw material tank 24 of the experimental ultrasonic atomizer 20. While the xylose aqueous solution whose temperature is controlled to 50° C. was circulating between the raw material tank 24 and the atomization tank 21 through the raw material supply pipe 25 and the return pipe 26, dehydration concentration by ultrasonic wave irradiation was performed for 0.5 hour in the batch operation. Then, as in the first example, the amount of liquid drops collected by the mist collector 29, the xylose concentration in the liquid drops, and the xylose concentration in the dehydrated and concentrated aqueous solution in the atomization tank 21 were measured.

(First Experimental Results)

Tables 1 and 2 show the results of the foregoing experiment.

TABLE 1

| | Examples | | | | | | |
|---|---|---|---|---|---|---|---|
| | 1 | 2 | 3 | 4 | 5 | 6 | 7 |
| Operation | Batch | Batch | Batch | Batch | Batch | Batch | Batch |
| Organic Compound A | Glycerol | Glycerol | Lactic Acid | Glucose | 1,2-propanediol | Xylose | hydroxymethylfurfural |
| Aqueous Solution Temperature in Atomization (° C.) | 60 | 50 | 50 | 50 | 50 | 50 | 50 |
| Atomization Time (hr.) | 9.0 | 2.5 | 6.0 | 1.0 | 0.5 | 0.4 | 1.5 |
| Amount of Supplied Aqueous Solution (g) | 841 | 804 | 805 | 800 | 504 | 801 | 600 |
| Concentration of A in Aqueous Solution (% by mass) | 48 | 59 | 44 | 62 | 51 | 42 | 51 |
| Amount of Liquid Drops Collected as Mist (g) | 413 | 83.8 | 414 | 54.8 | 27.4 | 73.0 | 58.2 |
| Concentration of A in Collected Liquid Drops (% by mass) | 0.19 | 0 | 0.64 | 0 | 0.91 | 0.91 | 0.11 |
| Concentration of A in Concentrated Aqueous Solution (% by mass) | 93 | 66 | 83 | 67 | 55 | 49 | 5.8 |

TABLE 2

| | Comparative Examples | | | | | | |
|---|---|---|---|---|---|---|---|
| | 1 | 2 | 3 | 4 | 5 | 6 | 7 |
| Operation | Batch | Batch | Batch | Batch | Batch | Batch | Batch |
| Organic Compound A | Glycerol | Lactic Acid | Lactic Acid | Glucose | Glycerol | 1,2-propanediol | Xylose |
| Aqueous Solution Temperature in Atomization (° C.) | 50 | 70 | 50 | 50 | 50 | 50 | 50 |
| Atomization Time (hr.) | 2.3 | 1.7 | 2.0 | 0.9 | 0.3 | 0.4 | 0.5 |
| Amount of Supplied Aqueous Solution (g) | 801 | 857 | 701 | 801 | 801 | 402 | 802 |
| Concentration of A in Aqueous Solution (% by mass) | 22 | 4.8 | 20 | 20 | 30 | 31 | 30 |
| Amount of Liquid Drops Collected as Mist (g) | 434 | 444 | 311 | 110 | 51.0 | 41.0 | 86.0 |
| Concentration of A in Collected Liquid Drops (% by mass) | 8.8 | 2.4 | 12 | 6.8 | 4.2 | 3.1 | 3.0 |
| Concentration of A in Concentrated Aqueous Solution (% by mass) | 36 | 8.2 | 26 | 24 | 32 | 34 | 34 |

The amount of liquid drops collected by the mist collector 29 was 413 g in the first example, 83.8 g in the second example, 414 g in the third example, 54.8 g in the fourth example, 27.4 g in the fifth example, 73.0 g in the sixth example, 58.2 g in the seventh example, 434 g in the first comparative example, 444 g in the second comparative example, 311 g in third comparative example, 110 g in the fourth comparative example, 51.0 g in the fifth comparative example, 41.0 g in the sixth comparative example, and 86.0 g in the seventh comparative example.

The concentration of the organic compound contained in the liquid drops collected by the mist collector 29 was a glycerol concentration of 0.19% by mass in the first example, a glycerol concentration of 0% by mass in the second example, a lactic acid concentration of 0.64% by mass in the third example, a glucose concentration of 0% by mass in the fourth example, a 1,2-propanediol concentration of 0.91% by mass in the fifth example, a xylose concentration of 0.91% by mass in the sixth example, a hydroxymethylfurfural concentration of 0.11% by mass in the seventh example, a glycerol concentration of 8.8% by mass in the first comparative example, a lactic acid concentration of 2.4% by mass in the second comparative example, a lactic acid concentration of 12% by mass in the third comparative example, a glucose concentration of 6.8% by mass in the fourth comparative example, a glycerol concentration of 4.2% by mass in the fifth comparative example, a 1,2-propanediol concentration of 3.1% by mass in the sixth comparative example, and a xylose concentration of 3.0% by mass in the seventh comparative example.

The concentration of the organic compound in the dehydrated and concentrated aqueous solution in the atomization tank 21 was a glycerol concentration of 93% by mass in the first example, a glycerol concentration of 66% by mass in the second example, a lactic acid concentration of 83% by mass in the third example, a glucose concentration of 67% by mass in the fourth example, a 1,2-propanediol concentration of 55% by mass in the fifth example, a xylose concentration of 49% by mass in the sixth example, a hydroxymethylfurfural concentration of 58% by mass in the seventh example, a glycerol concentration of 36% by mass in the first comparative example, a lactic acid concentration of 8.2% by mass in the second comparative example, a lactic acid concentration of 26% by mass in the third comparative example, a glucose concentration of 24% by mass in the fourth comparative example, a glycerol concentration of 32% by mass in the fifth comparative example, a 1,2-propanediol concentration of 34% by mass in the sixth comparative example, and a xylose concentration of 34% by mass in the seventh comparative example.

As will be seen from Tables 1 and 2, the first to seventh examples show a lower concentration of the organic compound contained in the collected liquid drops as compared to that in the first to seventh comparative examples. Thus, the aqueous solution of the organic compound is efficiently dehydrated and concentrated in the atomization tank 21. That is, a dehydration efficiency per energy in ultrasonic wave irradiation can be enhanced.

Second Experiment

Eighth Example

Glycerol was added to a glycerol aqueous solution containing glycerol at a concentration of 20% by mass to adjust the glycerol concentration of the resultant to 60% by mass. Then, a glycerol aqueous solution, whose concentration is adjusted to 60% by mass, of 300 g was supplied into the raw material tank 24 of the experimental ultrasonic atomizer 20, and a glycerol aqueous solution, whose concentration is adjusted to 60% by mass, of 200 g was supplied into the atomization tank 21. The temperature of the glycerol aqueous solution was controlled to 50° C., and the supply flow rate of the glycerol aqueous solution to be supplied from the raw material tank 24 to the atomization tank 21 is adjusted such that the supply speed thereof is 113 g/hr. Dehydration concentration by ultrasonic wave irradiation was performed for 1.0 hour in the semi-batch operation (Aspect 2A-(i)-a). Then, as in the first example, the amount of liquid drops collected by the mist collector 29, the glycerol concentration in the liquid drops, and the glycerol concentration in the dehydrated and concentrated aqueous solution in the atomization tank 21 were measured.

Ninth Example

A glycerol aqueous solution, whose glycerol concentration is 30% by mass, of 201 g was supplied into the raw material tank 24 of the experimental ultrasonic atomizer 20, and a glycerol aqueous solution, whose glycerol concentration is 60% by mass, of 251 g was supplied into the atomization tank 21. The temperature of the glycerol aqueous solution was controlled to 50° C. The supply flow rate of the glycerol aqueous solution to be supplied from the raw material tank 24 to the atomization tank 21 is adjusted such that the supply speed thereof is 37 g/hr, and therefore the glycerol concentration in the glycerol aqueous solution in the atomization tank 21 is maintained at equal to or greater than 40% by mass. Dehydration concentration by ultrasonic wave irradiation was performed for 1.1 hours in the semi-batch operation (Aspect 2B). Then, as in the first example, the amount of liquid drops collected by the mist collector 29, the glycerol concentration in the liquid drops, and the glycerol concentration in the dehydrated and concentrated aqueous solution in the atomization tank 21 were measured.

Tenth Example

Glycerol was added to a glycerol aqueous solution containing glycerol at a concentration of 20% by mass to adjust the glycerol concentration of the resultant to 60% by mass. Then, a glycerol aqueous solution, whose concentration is adjusted to 60% by mass, of 300 g was supplied into the raw material tank 24 of the experimental ultrasonic atomizer 20, and a glycerol aqueous solution, whose concentration is adjusted to 60% by mass, of 201 g was supplied into the atomization tank 21. The temperature of the glycerol aqueous solution was controlled to 50° C. The supply flow rate of the glycerol aqueous solution to be supplied from the raw material tank 24 to the atomization tank 21 is adjusted such that the supply speed thereof is 104 g/hr, and the recovery flow rate of the concentrated glycerol aqueous solution to be recovered from the atomization tank 21 is adjusted such that the discharge speed thereof is 74 g/hr. Dehydration concentration by ultrasonic wave irradiation was performed for 1.0 hour in the continuous operation (Aspect 3A-(i)-a). Then, as in the first example, the amount of liquid drops collected by the mist collector 29, the glycerol concentration in the liquid drops, and the glycerol concentration in the dehydrated and concentrated aqueous solution in the atomization tank 21 were measured.

Eleventh Example

A glycerol aqueous solution, whose glycerol concentration is 30% by mass, of 262 g was supplied into the raw material tank 24 of the experimental ultrasonic atomizer 20, and a glycerol aqueous solution, whose glycerol concentration is 60% by mass, of 251 g was supplied into the atomization tank 21. The temperature of the glycerol aqueous solution was controlled to 50° C. The supply flow rate of the glycerol aqueous solution to be supplied from the raw material tank 24 to the atomization tank 21 is adjusted such that the supply speed thereof is 40 g/hr, and the recovery flow rate of the concentrated glycerol aqueous solution to be recovered from the atomization tank 21 is adjusted such that the discharge speed thereof is 61 g/hr. Thus, the glycerol concentration in the glycerol aqueous solution in the atomization tank 21 is maintained at equal to or greater than 40% by mass. Dehydration concentration by ultrasonic wave irradiation was performed for 1.1 hours in the continuous operation (Aspect 3B). Then, as in the first example, the amount of liquid drops collected by the mist collector 29, the glycerol concentration in the liquid drops, and the glycerol concentration in the dehydrated and concentrated aqueous solution in the atomization tank 21 were measured.

(Second Experimental Results)
Table 3 shows the experimental results of the eighth to eleventh examples.

TABLE 3

| | Examples | | | |
|---|---|---|---|---|
| | 8 | 9 | 10 | 11 |
| Operation | Semi-Batch | Semi-Batch | Continuous | Continuous |
| Organic Compound A | Glycerol | Glycerol | Glycerol | Glycerol |
| Aqueous Solution Temperature in Atomization (° C.) | 50 | 50 | 50 | 50 |
| Atomization Time (hr.) | 1.0 | 1.1 | 1.0 | 1.1 |
| Amount of Aqueous Solution Supplied into Raw Material Tank (g) | 300 | 201 | 300 | 262 |
| Concentration of A in Aqueous Solution | 60 | 30 | 60 | 30 |

TABLE 3-continued

| | Examples | | | |
|---|---|---|---|---|
| | 8 | 9 | 10 | 11 |
| Supplied into Raw Material Tank (% by mass) | | | | |
| Amount of Aqueous Solution Supplied into Atomization Tank (g) | 200 | 251 | 201 | 251 |
| Concentration of A in Aqueous Solution Supplied into Atomization Tank (% by mass) | 60 | 60 | 60 | 60 |
| Supply Speed from Raw Material Tank to Atomization Tank (g/hr) | 113 | 37 | 104 | 40 |
| Discharge Speed from Atomization Tank (g/hr) | — | — | 74 | 61 |
| Amount of Liquid Drops Collected as Mist (g) | 18 | 16 | 26 | 21 |
| Concentration of A in Collected Liquid Drops (% by mass) | 0 | 0 | 0 | 0 |
| Concentration of A in Concentrated Aqueous Solution (% by mass) | 67 | 64 | 71 | 65 |

The amount of liquid drops collected by the mist collector 29 was 18 g in the eighth example, 16 g in the ninth example, 26 g in the tenth example, and 21 g in the eleventh example.

The concentration of the organic compound contained in the liquid drops collected by the mist collector 29 was a glycerol concentration of 0% by mass in the eighth example, a glycerol concentration of 0% by mass in the ninth example, a glycerol concentration of 0% by mass in the tenth example, and a glycerol concentration of 0% by mass in the eleventh example.

The concentration of the organic compound contained in the dehydrated and concentrated aqueous solution in the atomization tank 21 was a glycerol concentration of 67% by mass in the eighth example, a glycerol concentration of 64% by mass in the ninth example, a glycerol concentration of 71% by mass in the tenth example, and a glycerol concentration of 65% by mass in the eleventh example.

As will be seen from Table 3, in the case of dehydration concentration of the glycerol aqueous solution by ultrasonic wave irradiation in any of the semi-batch operation and the continuous operation, the glycerol concentration in the collected liquid drops is low. Thus, the glycerol aqueous solution is efficiently dehydrated and concentrated in the atomization tank 21.

INDUSTRIAL APPLICABILITY

The present invention is useful for the method for producing a concentrated aqueous solution of an organic compound and for the dehydration concentration method.

DESCRIPTION OF REFERENCE CHARACTERS 10, 20 Ultrasonic Atomizer
11, 21 Atomization Tank
12, 22 Ultrasonic Oscillator
13 Concentrated Aqueous Solution Discharge Pipe
14, 24 Raw Material Tank
15, 25 Raw Material Supply Pipe
16, 18, 26 Return Pipe
17 Organic-Compound-A Supply Pipe
19 Concentration Adjuster
27 Carrier Gas Supply Pipe
28 Mist Collecting Pipe
29 Mist Collector

The invention claimed is:

1. A method for producing a concentrated aqueous solution of an organic compound, comprising:
    a concentration adjustment step comprising adjusting an aqueous solution containing the organic compound at a concentration of less than 40% by mass to contain the organic compound at a concentration of equal to or greater than 40% by mass, the organic compound having two or more hydrophilic groups in a molecule; and
    a dehydration concentration water-removal step comprising irradiating the aqueous solution whose organic compound concentration is adjusted to equal to or greater than 40% by mass at the concentration adjustment step with an ultrasonic wave to atomize water.

2. The method of claim 1, wherein
    concentration adjustment is performed at the concentration adjustment step in such a manner that the aqueous solution containing the organic compound at the concentration of less than 40% by mass is mixed with the organic compound or an aqueous solution containing the organic compound at a concentration of greater than 40% by mass.

3. The method of claim 1, further comprising:
    a recovery step of recovering the concentrated aqueous solution of the organic compound formed by dehydration concentration at the water-removal step.

4. The method of claim 1, wherein
    said method for producing a concentrated aqueous solution of the organic compound is a batch operation.

5. The method of claim 1, wherein
    said method for producing a concentrated aqueous solution of the organic compound is a semi-batch operation in which
    the aqueous solution is formed, at the concentration adjustment step, in such a manner that the aqueous solution containing the organic compound at the concentration of less than 40% by mass is adjusted to contain the organic compound at the concentration of equal to or greater than 40% by mass is continuously or intermittently supplied to the aqueous solution of the organic compound which is to be dehydrated and concentrated at the water-removal step.

6. The method of claim 5, wherein
    the concentration adjustment of the concentration adjustment step for the aqueous solution to be continuously or intermittently supplied to the aqueous solution of the organic compound which is to be dehydrated and concentrated at the water-removal step is performed concurrently with the water-removal step in such a manner that the aqueous solution containing the organic compound at the concentration of less than 40% by mass is mixed with the aqueous solution containing the organic compound at the concentration of greater than 40% by mass.

7. The method of claim 6, wherein
    part or all of the aqueous solution containing the organic compound at the concentration of greater than 40% by mass is the concentrated aqueous solution of the organic compound formed by dehydration concentration at the water-removal step.

8. The method of claim 1, wherein
said method for producing a concentrated aqueous solution of the organic compound is a continuous operation in which
the aqueous solution is formed, at the concentration adjustment step, in such a manner that the aqueous solution containing the organic compound at the concentration of less than 40% by mass is adjusted to contain the organic compound at the concentration of equal to or greater than 40% by mass is continuously or intermittently supplied to the aqueous solution of the organic compound which is to be dehydrated and concentrated at the water-removal step, and
the concentrated aqueous solution of the organic compound is continuously or intermittently recovered.

9. The method of claim 1, wherein
the concentrated aqueous solution of the organic compound is produced by a semi-batch operation in which,
while the aqueous solution containing the organic compound at the concentration of less than 40% by mass is continuously or intermittently supplied to the aqueous solution of the organic compound which is to be dehydrated and concentrated at the water-removal step, the concentration adjustment step is performed in such a manner that a supply flow rate of the aqueous solution containing the organic compound at the concentration of less than 40% by mass is controlled such that the aqueous solution of the organic compound which is to be dehydrated and concentrated contains the organic compound at the concentration of equal to or greater than 40% by mass.

10. The method of claim 1, wherein
the concentrated aqueous solution of the organic compound is produced by a continuous operation in which,
while the aqueous solution containing the organic compound at the concentration of less than 40% by mass is continuously or intermittently supplied to the aqueous solution of the organic compound which is to be dehydrated and concentrated at the water-removal step, and the concentrated aqueous solution of the organic compound formed by dehydration concentration at the water-removal step is continuously or intermittently recovered, the concentration adjustment step is performed in such a manner that a supply flow rate of the aqueous solution containing the organic compound at the concentration of less than 40% by mass and a recovery flow rate of the concentrated aqueous solution are controlled such that the aqueous solution of the organic compound which is to be dehydrated and concentrated contains the organic compound at the concentration of equal to or greater than 40% by mass.

11. The method of claim 1, wherein
a temperature of the aqueous solution irradiated with the ultrasonic wave at the water-removal step is equal to or higher than 10° C. and equal to or lower than 100° C.

12. The method of claim 1, wherein
the organic compound has, as the hydrophilic groups, one or more chosen from a group consisting of a hydroxyl group, a carboxyl group, a carbonyl group, an ester group, an acetal group, a hemiacetal group, an ether group, an amino group, an ammonium group, an amide group, a sulfonate group, a sulfate ester group, a phosphonate group, a phosphate group, or an ureido group.

13. The method of claim 12, wherein
the organic compound contains polyhydric alcohol.

14. The method of claim 12, wherein
the organic compound contains an organic compound having a carboxyl group.

15. The method of claim 1, wherein
the molecule of the organic compound has equal to or greater than two carbon atoms and equal to or less than 22 carbon atoms.

16. The method of claim 1, wherein
a molecular weight of the organic compound is equal to or greater than 50 and equal to or less than 400.

17. The method of claim 1, wherein
the organic compound has, as the hydrophilic groups, one or more chosen from a group consisting of a hydroxyl group or a carboxyl group.

* * * * *